United States Patent
Wagner et al.

(10) Patent No.: US 11,643,667 B2
(45) Date of Patent: May 9, 2023

(54) MICROFLUIDIC LASER-ACTIVATED INTRACELLULAR DELIVERY SYSTEMS AND METHODS

(71) Applicant: CELLINO BIOTECH, INC., Cambridge, MA (US)

(72) Inventors: Matthias Wagner, Cambridge, MA (US); Marinna Madrid, Cambridge, MA (US)

(73) Assignee: CELLINO BIOTECH, INC., Cambridge, MA (US)

( * ) Notice: Subject to any disclaimer, the term of this patent is extended or adjusted under 35 U.S.C. 154(b) by 1289 days.

(21) Appl. No.: 16/115,140

(22) Filed: Aug. 28, 2018

(65) Prior Publication Data
US 2019/0071695 A1 Mar. 7, 2019

Related U.S. Application Data

(60) Provisional application No. 62/550,757, filed on Aug. 28, 2017, provisional application No. 62/701,863, filed on Jul. 23, 2018.

(51) Int. Cl.
| | |
|---|---|
| C12N 15/87 | (2006.01) |
| C12M 1/42 | (2006.01) |
| A61B 18/20 | (2006.01) |
| A61K 9/00 | (2006.01) |
| A61B 18/26 | (2006.01) |
| A61B 17/00 | (2006.01) |
| A61B 18/00 | (2006.01) |
| B82Y 5/00 | (2011.01) |
| H01S 3/00 | (2006.01) |

(52) U.S. Cl.
CPC .............. *C12N 15/87* (2013.01); *A61B 18/20* (2013.01); *A61B 18/26* (2013.01); *A61K 9/0009* (2013.01); *A61K 9/0019* (2013.01); *C12M 35/02* (2013.01); *A61B 2017/00765* (2013.01); *A61B 2018/00577* (2013.01); *A61B 2018/263* (2013.01); *B82Y 5/00* (2013.01); *H01S 3/00* (2013.01)

(58) Field of Classification Search
None
See application file for complete search history.

(56) References Cited

U.S. PATENT DOCUMENTS

| | | |
|---|---|---|
| 4,897,355 A | 1/1990 | Eppstein et al. |
| 4,946,787 A | 8/1990 | Eppstein et al. |
| 5,049,386 A | 9/1991 | Eppstein et al. |
| 5,795,755 A | 8/1998 | Lemelson |
| 5,900,374 A | 5/1999 | Otto-Nagels |
| 6,096,532 A | 8/2000 | Armstrong et al. |
| 6,153,400 A | 11/2000 | Matsumura et al. |
| 6,165,440 A | 12/2000 | Esenaliev |
| 6,673,008 B1 | 1/2004 | Thompson et al. |
| 8,492,140 B2 | 7/2013 | Smith et al. |
| 8,546,142 B2 | 10/2013 | Martin et al. |
| 9,181,529 B2 | 11/2015 | Kattman et al. |
| 9,499,780 B2 | 11/2016 | Smith et al. |
| 9,783,768 B2 | 10/2017 | Larcher et al. |
| 10,078,075 B2 | 9/2018 | Wikswo et al. |
| 10,829,729 B2 | 11/2020 | Mazur et al. |
| 10,876,086 B2 | 12/2020 | Suzuki et al. |
| 11,028,358 B2 | 6/2021 | Kelso et al. |
| 2002/0055166 A1 | 5/2002 | Cannon et al. |
| 2003/0040104 A1 | 2/2003 | Barbera-Guillem |
| 2003/0054335 A1 | 3/2003 | Taya et al. |
| 2003/0068814 A1 | 4/2003 | Malinge |
| 2004/0077073 A1 | 4/2004 | Schindler et al. |
| 2007/0163963 A1 | 7/2007 | Faustman et al. |
| 2008/0274529 A1 | 11/2008 | Dholakia et al. |
| 2009/0017543 A1 | 1/2009 | Wilkes et al. |
| 2009/0258417 A1 | 10/2009 | Tanaka et al. |
| 2009/0286317 A1 | 11/2009 | Demmler et al. |
| 2012/0130287 A1 | 5/2012 | Gruber |
| 2012/0171746 A1 | 7/2012 | Mazur et al. |
| 2012/0208273 A1 | 8/2012 | Tarunina et al. |
| 2012/0267515 A1 | 10/2012 | Wu et al. |
| 2012/0294836 A1 | 11/2012 | Rowley et al. |

(Continued)

FOREIGN PATENT DOCUMENTS

| | | |
|---|---|---|
| EP | 3556841 A1 | 10/2019 |
| KR | 20070012514 A | 1/2007 |

(Continued)

OTHER PUBLICATIONS

Breunig, et al. (2014) "High-Throughput Continuous Flow Femtosecond Laser-Assisted Cell Optoporation and Transfection", Microscopy Research and Technique, 77: 974-979.*

(Continued)

*Primary Examiner* — Robert M Kelly
(74) *Attorney, Agent, or Firm* — Wilson Sonsini Goodrich & Rosati

(57) ABSTRACT

An intracellular delivery system and method are provided. The intracellular delivery system comprises a laser-activated surface and cells positioned at a distance from the laser-activated surface. A laser provided a laser pulse that is used to porate membranes of the cells to deliver or extract cargo from the cells into a liquid surrounding the cells. The method of intracellular delivery comprises positioning a laser-activated surface at a distance from cells and applying a laser pulse from the laser to the surface to porate membranes of the cells to deliver or extract cargo from the cells into a liquid surrounding the cells.

20 Claims, 12 Drawing Sheets

(56) References Cited

U.S. PATENT DOCUMENTS

| | | |
|---|---|---|
| 2012/0329123 A1 | 12/2012 | Nakashima et al. |
| 2013/0102772 A1 | 4/2013 | Eshima et al. |
| 2013/0113140 A1 | 5/2013 | Gunn-Moore et al. |
| 2013/0169969 A1 | 7/2013 | Popescu et al. |
| 2015/0107995 A1 | 4/2015 | Sista et al. |
| 2015/0191744 A1 | 7/2015 | Wolfe et al. |
| 2015/0219543 A1 | 8/2015 | Yamauchi et al. |
| 2016/0177273 A1 | 6/2016 | Gong et al. |
| 2016/0195523 A1 | 7/2016 | Chatterjee et al. |
| 2016/0237392 A1 | 8/2016 | Lee |
| 2016/0355797 A1 | 12/2016 | Konermann et al. |
| 2017/0009252 A1 | 1/2017 | Baylink et al. |
| 2017/0014824 A1 | 1/2017 | Boyd et al. |
| 2017/0029864 A1 | 2/2017 | Straus |
| 2017/0081628 A1 | 3/2017 | Matsubara |
| 2017/0204407 A1 | 7/2017 | Gilbert et al. |
| 2018/0072975 A1 | 3/2018 | Aviles et al. |
| 2018/0087021 A1 | 3/2018 | Blanchard |
| 2019/0098559 A9 | 3/2019 | Kaur et al. |
| 2019/0169572 A1 | 6/2019 | Shi et al. |
| 2019/0352589 A1 | 11/2019 | Jing et al. |
| 2020/0087607 A1 | 3/2020 | Magnant |
| 2020/0141961 A1 | 5/2020 | Ahlfors |
| 2020/0200781 A1 | 6/2020 | Smith et al. |
| 2020/0208095 A1 | 7/2020 | Oram et al. |
| 2021/0123008 A1 | 4/2021 | Trainor et al. |
| 2021/0253991 A1 | 8/2021 | Kelso et al. |
| 2021/0261899 A1 | 8/2021 | Blanchard |
| 2021/0283606 A1 | 9/2021 | Thakkar et al. |
| 2021/0317399 A1 | 10/2021 | Nazareth et al. |
| 2021/0403942 A1 | 12/2021 | Wang et al. |
| 2022/0106549 A1 | 4/2022 | Magnant |
| 2022/0107488 A1 | 4/2022 | Berns et al. |
| 2022/0276463 A1 | 9/2022 | Hunt et al. |
| 2022/0282201 A1 | 9/2022 | Wagner et al. |
| 2022/0282202 A1 | 9/2022 | Wagner et al. |
| 2022/0282203 A1 | 9/2022 | Wagner et al. |
| 2022/0282223 A1 | 9/2022 | Wagner et al. |
| 2022/0284574 A1 | 9/2022 | Wagner et al. |

FOREIGN PATENT DOCUMENTS

| | | |
|---|---|---|
| WO | WO-2011132584 A1 | 10/2011 |
| WO | 2016/011070 A2 | 1/2016 |
| WO | 2016/011080 A2 | 1/2016 |
| WO | WO-2016109864 A1 | 7/2016 |
| WO | WO-2016114438 A1 | 7/2016 |
| WO | 2016/127069 A1 | 8/2016 |
| WO | 2017/023974 A1 | 2/2017 |
| WO | 2017062838 A1 | 4/2017 |
| WO | WO-2017079682 A1 | 5/2017 |
| WO | WO-2017208589 A1 | 12/2017 |
| WO | WO-2018085557 A1 | 5/2018 |
| WO | WO-2019046304 A1 | 3/2019 |
| WO | WO-2019178561 A2 | 9/2019 |
| WO | WO-2019241885 A1 | 12/2019 |
| WO | WO-2020033871 A1 | 2/2020 |
| WO | WO-2020097083 A1 | 5/2020 |
| WO | WO-2021150631 A1 | 7/2021 |
| WO | WO-2022096315 A1 | 5/2022 |
| WO | WO-2022192157 A1 | 9/2022 |

OTHER PUBLICATIONS

Balboa, 2015, Conditionaly stablized dCas9 activator for controlling gene expression in human cell reprogramming and differentiation, Stem Cell Reports 5:448-459.

Braun, 2017, Rapid and reversible epigenome editing by endogenous chromatin regulators, Nat Comm 8(1):560.

Chakraborty, 2014, A CRISPR/Cas9-Based System for Reprogramming Cell Lineage Specification, Stem Cell Reports 3(6):940-947.

Chavez, 2015, Highly efficient Cas9-mediated transcriptional programming. Nature Methods, 12(4):326-328.

Cheng, 2013, Multiplexed activation of endogenous genes by CRISPR-on, an RNA-guided transcriptional activator system, Cell Research 23(10):1163-1171.

Dominguez, 2015, Beyond editing: repurposing CRISPR-Cas9 for precition genome regulation and interrogation, Nat Rev Mol Cell Biol 17:5-15.

Genga, 2016, Controlling transcription in human pluripotent stem cells using CRISPR-effectors, Methods 101:36-42.

Gilbert, 2013, CRISPR-Mediated modular RNA-guided regulation of transcription in Eukaryotes, Cell 154(2):442-451.

Gilbert, 2014, Genome-Scale CRISPR-Mediated Control of Gene Repression and Activation, Cell, 159(3):647-661.

Hilton, 2015, Epigenome editing by a CRISPR-Cas9-based acetyltransferase activates genes from promoters and enhancers, Nat Biotech 33(5):510-517.

Horlbeck, 2016, Compact and highly active next-generation libraries for CRISPR-mediated gene repression and activation, eLife 5:914.

International Search Report and Written Opinion dated Oct. 29, 2018, for PCT/US18/48349, filed Aug. 28, 2018 (8 pages).

Joung, 2017, Genome-scale activation screen identifies a lncRNA locus regulating a gene neighbourhood, Nature 548(7667):343-346.

Joung, 2017, Genome-scale CRISPR-Cas9 knockout and transcriptional activation screening, Nature Protocols 12(4):828-863.

Kearns, 2014, Cas9 effector-mediated regulation of transcription and differentiation in human pluripotent stem cells, Development 141(1):219-223.

Kim, 2017, Highly efficient RNA-guided base editing in mouse embryos, Nat Biotech 35:435-437.

Konermann, 2015, Genome-scale transcriptional activation by an engineered CRISPR-Cas9 complex, Nature 517(7536):583-588.

Larson, 2013, CRISPR interference (CRISPRi) for sequence-specific control of gene expression, Nature Protocols, 8(11):2180-2196.

Liao, 2017, In Vivo Target Gene Activation via CRISPR/Cas9-Mediated Trans-epigenetic Modulation, Cell 171(7):1495-1507.

Liu, 2018, CRISPR-Based chromatin remodeling of the endogenous Oct4 or Sox2 locus enables reprogramming to pluripotency. Cell Stem Cell 22:252-261.

Mali, 2013, CAS9 transcriptional activators for target specificity screening and paired nickases for cooperative genome engineering, Nat Biotech 31(9):833-838.

Mircetic, 2017, Purified Cas9 fusion proteins for advanced genome manipulation, Small Methods 1(4).

Qi, 2013, Repurposing CRISPR as an RNA-Guided platform for sequence-specific control of gene expression, Cell 152(5):1173-1183.

Rees, 2017, Improving the DNA specificity and applicability of base editing through protein engineering and protein delivery, Nat Comm 8:15790.

Saklayen, 2017, Intracellular delivery using nanosecond-laser excitation of large-area plasmonic substrates, ACS Nano 11:3671-3680.

Tak, 2017, Inducible and multiplex gene regulation using CRISPR-Cpf1-based transcription factors, Nat Meth 14(12):1163-1166.

Tanenbaum, 2014, A Protein-tagging system for signal amplification in gene expression and fluorescence imaging, Cell 159(3):635-646.

Weltner, 2018, Human pluripotent reprogramming with CRISPR activators, Nat Comm 9:2643.

Antkowiak et al.: Fast targeted gene transfection and optogenetic modification of single neurons using femtosecond laser irradiation. Sci Rep. 3:3281 doi:10.1038/srep03281 [1-8] (2013).

Baffou et al.: Super-Heating and Micro-Bubble Generation around Plasmonic Nanoparticles under cw Illumination. J. Phys. Cherm. C. 118(9):4890-4898 (2014).

Cahan et al., CellNet: Network Biology Applied to Stem Cell Engineering. Cell 158(4):903-915 (2014).

Chakravarty et al.: Delivery of molecules into cells using carbon nanoparticles activated by femtosecond laser pulses. Nat. Nanotechnol. 5(8):607-611 (2010).

Chen et al.: Dynamics of transient microbubbles generated by fs-laser irradiation of plasmonic micropyramids. Appl. Phys. Lett. 110, 153102 doi:10.1063/1.4979886 [1-6] (2017).

(56) References Cited

OTHER PUBLICATIONS

Chiu et al.: Universally applicable three-dimensional hydrodynamic microfluidic flow focusing. Lab Chip. 13(9):1803-1809 (2013).
Courvoisier et al.: Plasmonic Tipless Pyramid Arrays for Cell Poration. Nano Lett. 15(7):4461-4466 (2015).
European Application No. 18850702.4 Extended European Search Report dated May 7, 2021.
Fan et al.: Laser-induced microbubble poration of localized single cells. Lab Chip. 14(9):1572-1578 (2014).
Graf et al.: Imaging and analysis of three-dimensional cell culture models. Methods Mol Biol 591:211-227 (2010).
Kiani et al.: Cas9 gRNA engineering for genome editing, activation and repression. Nat Methods 12(11):1051-1054 (2015).
Le Gac et al.: Sonoporation of suspension cells with a single cavitation bubble in a microfluidic confinement. Lab Chip. 7(12):1666-1672 (2007).
Liu et al.: Formation and dissolution of microbubbles on highly-ordered plasmonic nanopillar arrays. Sci Rep. 5:18515 doi:10.1038/srep18515 [1-9] (2015).
Lukianova-Hleb et al., Multifunctional Cell Processing with Plasmonic Nanobubbles. International Scholarly and Scientific Research and Innovation 7(11): 677-681 (2013).
Manno et al., Molecular Diversity of Midbrain Development in Mouse, Human and Stem Cells. Cell 167(2):566-580 (2016).
Morales et al.: Affinity-Based Assembly of Peptides on Plasmonic Nanoparticles Delivered Intracellularly with Light Activated Control. Bioconjug Chem. 28(7):1816-1820 (2017).
Mulholland et al.: Cell loading with laser-generated stress waves: The role of the stress gradient. Pharm Res. 16(4):514-518 (1999).
Park et al.: Transient temperature during the vaporization of liquid on a pulsed laser-heated solid surface. J. Heat Transfer 118(3):702-708 (1996).
PCT/US2019/045969 International Search Report and Written Opinion dated Nov. 8, 2019.
Petka et al.: Reversible Hydrogels from Self-Assembling Artificial Proteins. Science 281(5375):389-392 (1998).
Pitsillides et al.: Selective cell targeting with light-absorbing microparticles and nanoparticles. Biophys. J. 84(6):4023-4032 (2003).
Quinto-Su et al.: Generation of laser-induced cavitation bubbles with a digital hologram. Optics Express 16(23):18964-18969 (2008).
Shmakov et al. Discovery and Functional Characterization of Diverse Class 2 CRISPR-Cas Systems. Mol Cell 60(3):385-397 (2015).
Stevenson et al.: Femtosecond optical transfection of cells: viability and efficiency. Opt Express 14(16):7125-7133 (2006).
Stewart et al.: Intracellular Delivery by Membrane Disruption: Mechanisms, Strategies, and Concepts. Chem. Rev 118(16): 7409-7531 (2018).
Tam et al.: Profile of laser-produced acoustic pulse in a liquid. IBM Research Laboratory, Research Report [1-28] (1983).
Tang et al.: Efficient delivery of small interfering RNA to plant cells by a nanosecond pulsed laser-induced stress wave for post-transcriptional gene silencing. Plant Sci. 171(3):375-381 (2006).
Timko et al.: Near-infrared-actuated devices for remotely controlled drug delivery for remotely controlled drug delivery. Proc Natl Acad Sci USA 111(4):1349-1354 (2014).
Vogel et al.: Acoustic transient generation by laser-produced cavitation bubbles near solid boundaries. J. Acoust. Soc. Am. 84(2):719-731 doi:10.1121/1.396852 (1988).
Vogel et al.: Energy balance of optical breakdown in water at nanosecond to femtosecond time scales. Appl. Phys. B 68:271-280 (1999).
Vogel et al.: Shock wave emission and cavitation bubble generation by picosecond and nanosecond optical breakdown in water. J. Acoust. Soc. Am. 100(1):148-165 doi:10.1121/1.415878 (1996).
Williams: A possible alteration in the permeability of ascites cell membranes after exposure to acoustic microstreaming. J. Cell Sci. 12(3):875-885 (1973).
Wu et al.: Pulsed laser triggered high speed microfluidic fluorescence activated cell sorter. Lab Chip. 12(7):1378-1383 (2012).
Yin et al.: Engineering Stem Cell Organoids 18(1):25-38 (2016).

Zhou et al.: Controlled permeation of cell membrane by single bubble acoustic cavitation. J. Controlled Release 157(1):103-111 (2012).
International Search Report and Written Opinion of the International Searching Authority dated Oct. 29, 2018 for International Application No. PCT/US2018/048349, nine (9) pages.
U.S. Appl. No. 17/688,837 Final Office Action dated Oct. 5, 2022.
U.S. Appl. No. 17/688,857 Final Office Action dated Oct. 14, 2022.
U.S. Appl. No. 17/688,859 Final Office Action dated Sep. 27, 2022.
U.S. Appl. No. 17/688,861 Final Office Action dated Nov. 7, 2022.
Aasen et al.: Isolation and cultivation of human keratinocytes from skin or plucked hair for the generation of induced pluripotent stem cells. Nat Protoc. 2010 5(2):371-382 doi:10.1038/nprot.2009.241 (2010).
Ahmed et al.: In situ self-assembly of gold nanoparticles on hydrophilic and hydrophobic substrates for influenza virus-sensing platform. Sci Rep. 7:44495: 1-11 doi:10.1038/srep44495 (2017).
Ban et al.: Efficient generation of transgene-free human induced pluripotent stem cells (iPSCs) by temperature-sensitive Sendai virus vectors. Proc Natl Acad Sci USA 108(34):14234-14239 doi:10.1073/pnas.1103509108 (2011).
Bar-Nur et al. Epigenetic memory and preferential lineage-specific differentiation in induced pluripotent stem cells derived from human pancreatic islet Beta cells. Cell Stem Cell 9:17-23 (2011).
Chen et al.: Nanofabrication by electron beam lithography and its applications: A review. Microelectronic Engineering 135:57-72 https://doi.org/10.1016/j.mee.2015.02.042 (2015).
Drews et al.: The cytotoxic and immunogenic hurdles associated with non-viral mRNA-mediated reprogramming of human fibroblasts. Biomaterials 33(16):4059-4068 doi:10.1016/j.biomaterials.2012.02.025 (2012).
Drozd et al., Generation of Human iPSCs From Cells of Fibroblastic and Epithelial Origin by Means of the oriP/EBNA-1 Episomal Reprogramming System. Stem Cell Res Ther 6 (1): 122 (2015).
EP Application No. 19846753.2 Extended European Search Report dated May 31, 2022.
Gill et al.: Progress and prospects: the design and production of plasmid vectors. Gene Ther. 16(2):165-171 doi:10.1038/gt.2008.183 (2009).
He et al.: Single-shot aperture-scanning Fourier ptychography. Opt Express 26(22):28187-28196 doi:10.1364/OE.26.028187 (2018).
Hu et al.: Fluorescence in situ hybridization (FISH): an increasingly demanded tool for biomarker research and personalized medicine. Biomark Res. 2:3:1-13 doi:10.1186/2050-7771-2-3 (2014).
Hudin et al.: Localized Tactile Stimulation by Time-Reversal of Flexural Waves: Case Study With a Thin Sheet of Glass. IEEE World Haptics Conference, pp. 1-6 DOI:10.1109/WHC.2013.6548386 (2013).
Jingshan et al.: Transport of Intensity phase imaging by intensity spectrum fitting of exponentially spaced defocus planes. Opt Express. 22(9):10661-10674 doi:10.1364/OE.22.010661 (2014).
Jo et al.: Quantitative Phase Imaging and Artificial Intelligence: A Review. IEEE Journal of Selected Topics in Quantum Electronics 25(1):1-14 (2019).
Kashyap et al.: Selective local lysis and sampling of live cells for nucleic acid analysis using a microfluidic probe. Sci Rep. 6:29579:1-10 doi:10.1038/srep29579 (2016).
Kim et al.: Generation of human induced pluripotent stem cells by direct delivery of reprogramming proteins. Cell Stem Cell 5;4(6):472-476 doi:10.1016/j.stem.2009.05.005 (2009).
Kim et al.: Generation of human induced pluripotent stem cells from osteoarthritis patient-derived synovial cells. Arthritis Rheum 63(10):3010-3021 doi:10.1002/art.30488 (2011).
Lee et al.:Single-shot phase retrieval via Fourier ptychographic microscopy. Optica 5(8):976-983 https://doi.org/10.1364/OPTICA.5.000976 (2018).
Li et al.: Excitable networks controlling cell migration during development and disease. Semin Cell Dev Biol. 100:133-142 doi:10.1016/j.semcdb.2019.11.001 (2020).
Loh, et al. Reprogramming of T Cells from Human Peripheral Blood. Cell Stem Cell. Jul. 2, 2010; 7(1): 15-19.

(56) References Cited

OTHER PUBLICATIONS

Lopatynskyi et al.: Au nanostructure arrays for plasmonic applications: annealed island films versus nanoimprint lithography. Nanoscale Res Lett. 10:99: 1-9 doi:10.1186/s11671-015-0819-1 (2015).
Mann: Rapid isolation of antigen-specific clones from hybridoma fusions. Nat Methods 4, i-ii URL:https://doi.org/10.1038/nmeth1028 (2007).
Okita et al.: A more efficient method to generate integration-free human iPS cells. Nat Methods 8(5):409-412 doi:10.1038/nmeth.1591 (2011).
Okita et al.: Generation of mouse-induced pluripotent stem cells with plasmid vectors. Nature Protocols 5(3):418-428 (2010).
PCT/US2022/019196 International Search Report and Written Opinion dated Jun. 1, 2022.
Rim et al.: Chondrogenic Differentiation from Induced Pluripotent Stem Cells Using Non-Viral Minicircle Vectors. Cells 9(3):582:1-21 doi:10.3390/cells9030582 (2020).
Sanchez-Esquivel et al.: Spectral dependence of nonlinear absorption in ordered silver metallic nanoprism arrays. Sci Rep. 7(1):5307:1-9 doi:10.1038/s41598-017-04814-2 (2017).
Segalman: Patterning with block copolymer thin films. Materials Science and Engineering R Reports 48(6):191-226 DOI:10.1016/j.mser.2004.12.003 (2005).
Skorik et al.: Xeno-Free Reprogramming of Peripheral Blood Mononuclear Erythroblasts on Laminin-521. Curr Protoc Stem Cell Biol. 52(1):e103:1-41 doi:10.1002/cpsc.103 (2020).
Stewart et al.: Intracellular Delivery by Membrane Disruption: Mechanisms, Strategies, and Concepts. Chem Rev. 118(16):7409-7531 doi:10.1021/acs.chemrev.7b00678 (2018).
Takahasi et al.: Induction of pluripotent stem cells from adult human fibroblasts by defined factors. Cell 131(5):861-872 doi:10.1016/j.cell.2007.11.019 (2007).
Thiers: Dermatology and Dermatologic Surgery. Chapter 15—Miscellaneous Topics in Clinical Dermatology, Elsevier—Health Sciences Division, pp. 302-303 (2008).
Tvarozek et al.: Plasmonic behaviour of sputtered Au nanoisland arrays. Applied Surface Science 395:241-247 DOI:10.1016/j.apsusc.2016.04.183 (2017).
U.S. Appl. No. 16/115,140 Non-Final Office Action dated Jul. 29, 2022.
U.S. Appl. No. 17/688,837 Non-Final Office Action dated May 26, 2022.
U.S. Appl. No. 17/688,854 Non-Final Office Action dated May 11, 2022.
U.S. Appl. No. 17/688,857 Non-Final Office Action dated Jun. 9, 2022.
U.S. Appl. No. 17/688,859 Non-Final Office Action dated Jun. 10, 2022.
U.S. Appl. No. 17/688,861 Non-Final Office Action dated Jun. 24, 2022.
Warren et al., Highly efficient reprogramming to pluripotency and directed differentiation of human cells with synthetic modified mRNA. Cell Stem Cell 7(5):618-630 (2010).
Watt et al.: Ion beam lithography and nanofabrication: A review. International Journal of Nanoscience 4(3):269-286 DOI:10.1142/S0219581X05003139 (2005).
Yoshioka et al.: Efficient generation of human iPSCs by a synthetic self-replicative RNA. Cell Stem Cell 13(2):246-254 doi:10.1016/j.stem.2013.06.001 (2013).
Zheng et al.: Concept, implementations and applications of Fourier ptychography. Nature Physics Reviews 3(3):207-223 DOI:10.1038/s42254-021-00280-y (2021).
Zhou et al.: Generation of induced pluripotent stem cells from urine. J Am Soc Nephrol. 22(7):1221-1228 doi:10.1681/ASN.2011010106 (2011).
Zhou et al.: Integration-free Methods for Generating Induced Pluripotent Stem Cells. Genomics, Proteomics & Bioinformatics 11(5):284-287 (2013).
Zhou et al.: Si surface passivation by $SiO_x$ : H films deposited by a low-frequency ICP for solar cell applications. Journal of Physics D Applied Physics 45(39):395401, pp. 1-8 DOI:10.1088/0022-3727/45/39/395401 (2012).
Zou et al.: High-resolution transport-of-intensity quantitative phase microscopy with annular illumination. arXiv:1704.04091v3 [physics.optics], pp. 1-25 doi:10.48550/ARXIV.1704.04091 (2017).
Zou et al.: High-resolution transport-of-intensity quantitative phase microscopy with annular illumination. Sci Rep. 7(1):7654, pp. 1-22 doi:10.1038/S41598-017-06837-1 (2017).
Zuo et al.: Transport of intensity equation: a tutorial. Optics and Lasers in Engineering 135(106187):1-98 URL:https://doi.org/10.1016/j.optlaseng.2020.106187 (2020).
U.S. Appl. No. 18/061,811 Non-Final Office Action dated Jan. 12, 2023.

\* cited by examiner

MICROFLUIDIC LASER-ACTIVATED INTRACELLULAR DELIVERY SYSTEMS AND METHODS

CROSS-REFERENCE TO RELATED APPLICATIONS

This application claims priority to and the benefit of U.S. Provisional Application No. 62/701,863 filed Jul. 23, 2018 and U.S. Provisional Application No. 62/550,757 filed Aug. 28, 2017, the contents of which are incorporated by reference herein in their entirety.

TECHNICAL FIELD

The invention generally relates to intracellular delivery systems, particularly laser-activated intracellular delivery systems.

BACKGROUND

Most individuals in the world's population suffer from at least one health problem or disease. Treatment can be costly and long in duration, when treatment methods and drugs or therapeutics are available. Treatment of diseases and health conditions with drugs, therapeutics, and genetic therapy is more efficient when the drug, therapeutic, or gene is delivered to the cells of the individual. Delivery within cells is known as intracellular delivery and is a method used for several medical applications. Though several methods of physical intracellular delivery have been studied, current intracellular delivery methods have several disadvantages.

SUMMARY

A laser-triggered intracellular delivery system provides a consistent and efficient method for intracellular delivery and extraction. By providing a system comprising a laser-activated surface, target cells positioned at a distance from the laser-activated surface, and a laser that provides laser pulses, the present system allows for permeation of the cell membranes. By porating the cell membranes, the system allows for intracellular delivery of cargo into cells or extraction of cargo from the cells. The target cells may be stationary in a medium or may be continuously flowing at a distance from the laser-activated surface.

In some instances, microbubbles are produced by the system for purposes of intracellular delivery. In particular, the laser-triggered intracellular delivery system produces bubbles that are consistent in spacing and size, which also allows for spacing between bubbles that are relatively dense in order to achieve multiple sites, or multiple bubbles, per cell. By producing the bubbles with a minimum amount of energy, the invention processes the maximum number of cells simultaneously, thereby leading to efficient absorption of laser light and promotion of bubble nucleation. For example, in an embodiment, the present invention uses bubbles explosively formed on a surface by using a pulsed light source. By using the laser-activated surface to create the microbubbles, the cells are not directly exposed to high-intensity laser light.

The invention efficiently delivers molecular cargo and is manufacturable using standard, low-cost processes. Any suitable low-cost process may be used for manufacturing, such as micromachining processes. Preferably microreplication techniques are used for manufacturing. The invention is compatible with standard research and development formats, such as well plates used in research, and is extensive to high-volume formats used in manufacturing, such as bioprocessing. Furthermore, the invention is scalable. For example, the target cell may be one particular cell, hundreds of cells, thousands of cells, or more, such as may be required for bulk processing. For example, bulk processing may be possible when the invention is used with continuously flowing cells.

Certain aspects of the invention are directed to an intracellular delivery system. The intracellular delivery system comprises a laser-activated surface; cells positioned at a distance from the laser-activated surface; and a laser providing a laser pulse. The laser pulse porates membranes of the cells to deliver or extract cargo from the cells into a liquid surrounding the cells. The laser pulse is converted from optical energy into mechanical energy in the form of a pressure wave. The pressure wave allows for delivery or extraction of cargo from the cells, thereby allowing intracellular delivery. Further, cells flow into and out of a space adjacent to the laser-activated surface. The cells may flow in a continuous flow. The cells may be stationary on a surface, or have "stopped" flow.

Any suitable cargo may be delivered or extracted from the cells. In some embodiments, cargo delivered is initially confined to a layer within liquid adjacent to the laser-activated surface and adjacent to a cell layer.

In some embodiments, the laser-activated surface is selectively targeted to porate specific cells in the adjacent volume. In some instances, the laser-activated surface is spatially targeted. In some instances, the laser-activated surface is temporally targeted. In certain embodiments, transport of cargo into or out of the cells subsequent to poration is promoted by one or more of additional laser pulses, electric fields, turbulent flow, or thermal pulses.

In some embodiments, the intracellular delivery system further comprises contrast-agent type microbubbles. The contrast-agent type microbubbles are added to the liquid surrounding the cells. For example, a first set of microbubbles is laser-generated and then imploded by a second set of laser-generated bubbles. The addition of gas-filled layers or structures in proximity to the cells enhances the effect of the laser-activated bubbles, allowing the laser-activated surfaces to be further removed from the cells themselves, making the delivery more consistent over a range of conditions, and allowing further optimization of the mechanical conditions surrounding the cells. In some embodiments of the present invention, the supplementary gas bubbles may be coated with cargo molecules or constructs to be delivered into cells, and the optically-activated bubbles are used to completely disrupt/collapse the supplementary bubbles, and potentially create liquid jetting, upon which the attached cargos diffuse through or are jet-delivered through the cell membranes.

In some embodiments, the laser pulse is provided by an optical source comprising diode-pumped solid state lasers, lamp-pumped solid state lasers, gas lasers, fiber lasers, diode lasers, or quantum cascade lasers. For example, the laser pulse may be provided by a continuous wave laser. The laser pulse may be produced from any suitable light source, such as a Q-switched, directly modulated, or chopped/redirected light source.

The cargo delivered or extracted may be selected from the group consisting of Cas9, TALEN, ZFN, Guide RNA, ssODN, mRNA, pre-mRNA, BACs, PNA, pDNA, chromosomes, mitochondria, siRNA, shRNA, miRNA, proteins, morpholinos, metabolites, small molecules, peptides, anitbodies, nanobodies, carbon nanotubes, fluorescent tags and/ or dyes, molecular beacons, DNA origami, nanodevices, MEMS devices, polymer constructs including controlled compound release structures (such as polymersome nanoparticles), metal or other functional nanoparticles, nuclei, subcellular organelles, ribozymes, enzymes, microbial pathogens, microbeads, surface Raman-enhanced particles, quantum dots, radionuclide, and magnetic beads.

In some embodiments, the laser-activated surface is patterned. For example, the laser-activated surface comprises a patterned layer of material selected from the group consisting of a thin layer of metal, polymer materials, ink-containing polymers, and an oxide layer.

Certain aspects of the invention are directed to a method of intracellular delivery. The method comprises positioning a laser-activated surface at a distance from cells and applying a laser pulse to the surface to permeate membranes of the cells to deliver or extract cargo from the cells into a liquid surrounding the cells. The laser pulse is translated from optical energy into mechanical energy in the form of a pressure wave.

In some embodiments, the cells flow into and out of a space adjacent to the laser-activated surface. The cells may flow in a continuous flow over the laser-activated surface. The cells may be stationary on the laser-activated surface.

In some examples, the cargo delivered is initially confined to a layer within liquid adjacent to the laser-activated surface and adjacent to a cell layer. The transport of cargo into or out of the cells subsequent to poration may be promoted by applying additional laser pulses, electric fields, turbulent flow, or thermal pulses. In some embodiments, the method further comprises selectively targeting the laser-activated surface to porate specific cells. The laser-activated surface is spatially targeted. The laser-activated surface is temporally targeted.

In some embodiments, the method further comprises adding contrast-agent type microbubbles to the liquid surrounding the cells. For example, the method may further comprise laser-generating a first set of microbubbles and then imploding the first set of microbubbles by a second set of laser-generated bubbles.

DETAILED DESCRIPTION

Figure 1:
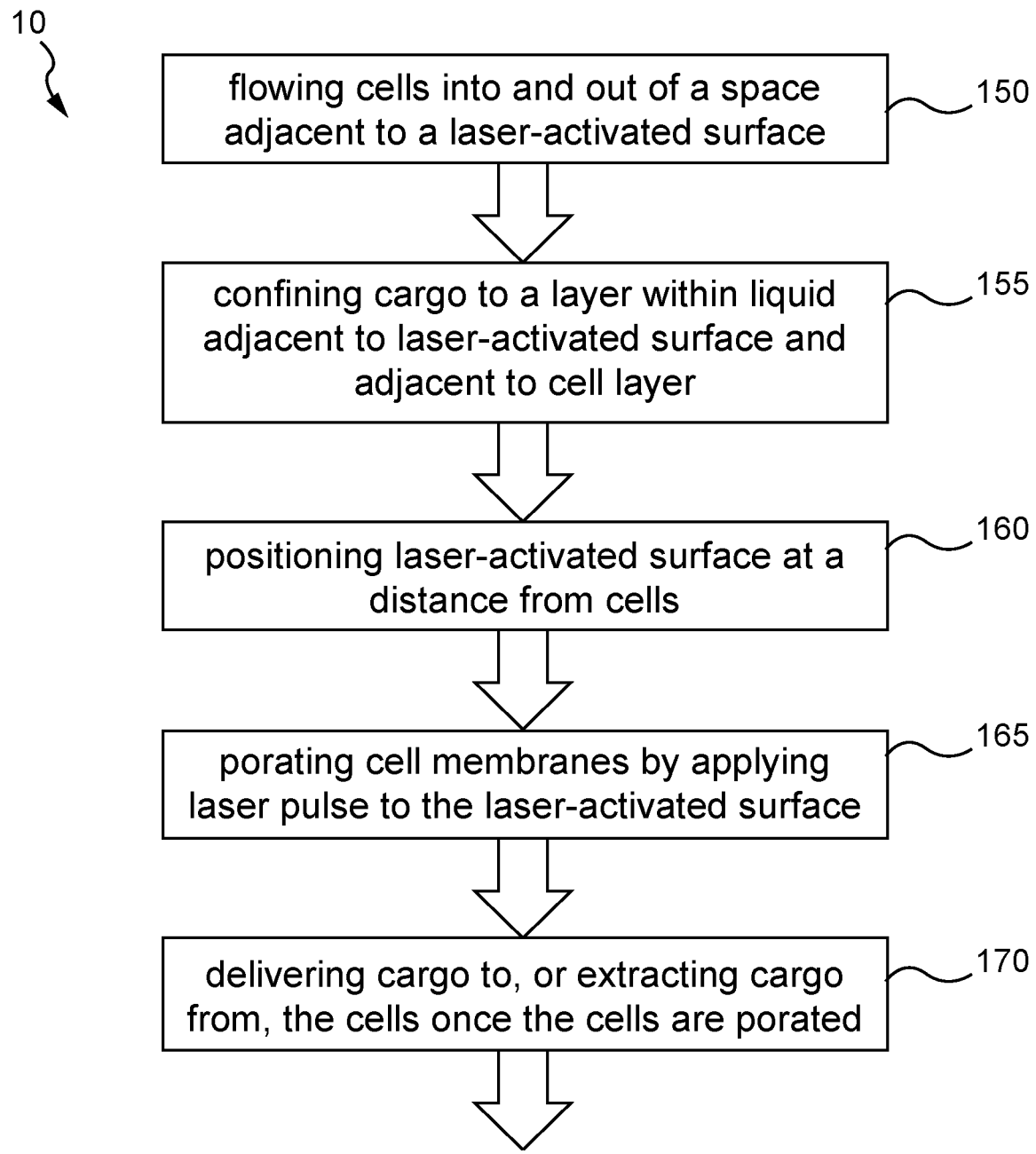
FIG. 1 diagrams a method according to the present invention.

FIG. 1 diagrams a method 10 according to the present invention. The method includes flowing cells into and out of a space adjacent to a laser-activated surface 150. The cargo may be confined to a layer within liquid adjacent to the laser-activated surface and adjacent to a cell layer 155. The laser-activated surface is positioned at a distance from the cells 160. The cell membranes may be porated by applying the laser pulse to the laser-activated surface 165. Once the cell membranes are porated, cargo may be delivered into, or extracted from, the cells 170.

In some embodiments, the present invention may incorporate features from other methods of physical intracellular delivery, such as features described in "In vitro and ex vivo strategies for intracellular delivery", Stewart et al, Nature (2016), which is incorporated by reference herein. For example, features related to the use of transient mechanical force may be applied to cell membranes for the purpose of stressing the membrane and creating temporary openings through which molecular cargoes may be delivered, or cellular contents may be extracted.

Figure 2:
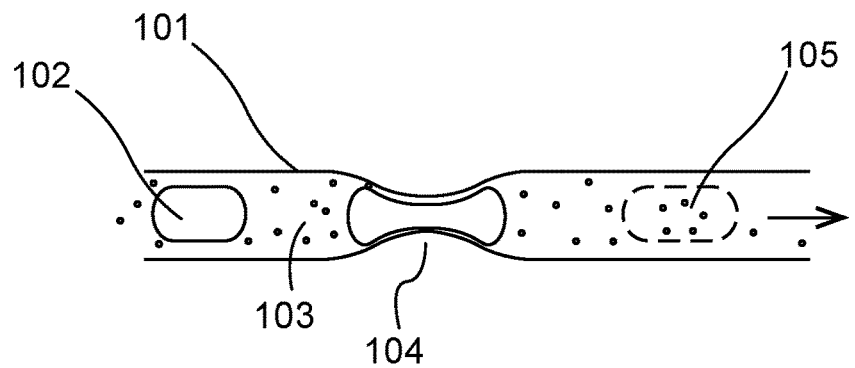
FIG. 2 shows an example of a cell squeezing method where transient forces are applied to a cell membrane.

FIG. 2 shows an example of a method that was developed for applying transient forces to a cell membrane. A pressure differential is applied over a microfluidic channel 101 in order to push cells 102 in a medium 103 which contains the cargo to be delivered through one or more constrictions 104.

The forces that arise cause pores to form in the cell membrane that last for up to 20 seconds, allowing the cargo to diffuse into the cell as shown by 105. The system is simple in its construction, but suffers from a number of drawbacks: the pressure required to drive cells through sufficiently small constrictions is very high, and results in difficult system requirements; the narrow channels and constrictions make the system prone to clogging and/or require complex pre-processing in order to filter out larger particles and ensure only single cells travel through the channel; the constriction size (cross-sectional area and length) is highly specific to certain cell size, shape and orientation, and may not produce the intended effect if there is variation in these parameters; and the rapid flow system is not suitable in general to certain sensitive cell types. Nevertheless, the system has been used to successfully deliver cargos to cells in a number of applications.

A flow-based system would be able to apply forces to cell membranes without requiring such a narrow constriction, thereby reducing pressure requirements and eliminating or mitigating clogging issues.

Figure 3:
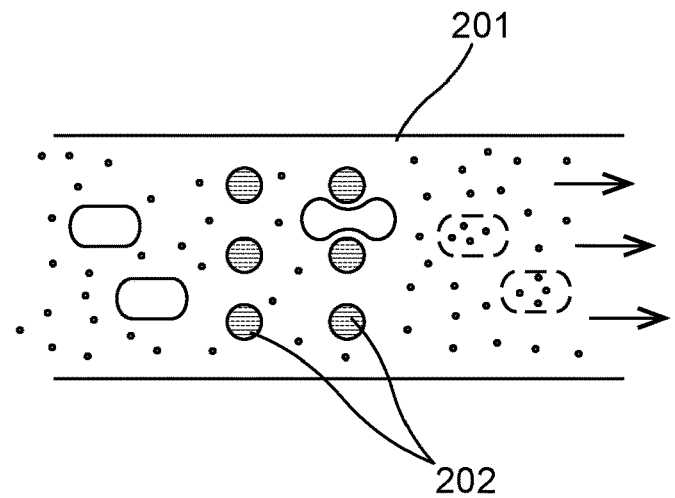
FIG. 3 shows an example of a cell squeezing method where a channel contains flow obstructions that cause local flow perturbations, opening up pores in the membranes and allowing exogenous materials in the flow to be introduced into the cells.

FIG. 3 shows a method where a channel 201 is contains flow obstructions 202 that cause local flow perturbations, resulting in local pressure changes that stress cell membranes, opening up pores in the membranes and allowing exogenous materials in the flow to be introduced into the cells. By providing a more "open" format than the preceding single-channel/single-constriction architecture, the inventor has sought to alleviate of the clogging issues described above. This occurs, however, at the expense of less uniformity in the stresses experienced by cells (depending on their position in the flow, shape, orientation, etc.). Moreover, the physical obstructions in the channel still present the risk of clogging, or will require cells to be greatly spaced out in the flow—which in turn requires a large amount of medium, and therefore cargo, which can in many cases be rare and/or expensive. One approach to a more robust microfluidic shearing system is described in "A method for mechanical and hydrodynamic microfluidic transfection and apparatus therefor", Ryan PAWELL (PCT/AU2015/050748), which is hereby incorporated in its entirety by reference.

Using direct mechanical methods such as scraping, squeezing, and shearing cells for the purpose of disrupting their membranes is effective, but often inconsistent and/or damaging to cells. A more indirect method of cell membrane permeation is the use of pressure waves to stress the membrane. This method has advantages because the method does not require physical obstruction (and possibly damaging contact) of the cell, and does not require high flow speed systems—so is potentially applicable to a wider range of cells.

In some embodiments, the present invention may incorporate features related to the permeating effect of acoustic or pressure waves, such as described in "A Possible Alteration in the Permeability of Ascites Cell Membranes after Exposure to Acoustic Microstreaming", A. R. WILLIAMS, J. Cell Sci., 1973, 12:875-885, which is hereby incorporated by reference. For example, features may include using ultrasound transducers to directly create pressure waves in order to alter cell membrane properties or using ultrasonic transducers to produce cavitation, which in turn produces very intense shockwaves.

Features that extend beyond the use of conventional ultrasonic transducers (such as piezoelectric devices) may also be used in the present invention. For example, features may include using intense laser pulses to create bubbles in liquid by a number of mechanisms. The growth and collapse of the bubbles cause intense pressure waves and differentials in the medium, such as described in "Profile of laser-produced acoustic pulse in a liquid", B. Sullivan and A. C. Tam, J. Acoust. Soc. Am., 1984, 75, 437-441; "Acoustic transient generation by laser-produced cavitation bubbles near solid boundaries", Vogel and W. Lauterborn, J. Acoust. Soc. Am., 1988, 84, 719-731; and "Shock wave emission and cavitation bubble generation by picosecond and nanosecond optical breakdown in water", Vogel et al, J. Acoust. Soc. Am., 1996, 100 (1), 148-165, which are hereby incorporated by reference.

Furthermore, features related to effects of solid surfaces in the proximity of the bubbles, including the potential to achieve stronger shockwaves (and therefore higher transient pressure differentials) may be used in embodiments of the invention. For example, pulsed lasers may be used to form bubbles in liquid by focusing laser light within the liquid volume. The power and energy threshold for bubble formation with light focused in water or a similar medium is quite high, requiring power levels on the order of $10^{11}$ W/cm$^2$, and fluences on the order of 10 J/cm$^2$ for picosecond pulsed lasers, and 500 J/cm$^2$ for nanosecond-pulsed lasers at 1064 nm, as described in "Energy balance of optical breakdown in water at nanosecond to femtosecond time scales", Vogel et al, Appl. Phys. B, 1999, 68, 271-280, herein incorporated by reference. At shorter wavelengths, the energy and power requirements are typically higher because of the low absorption of water in this regime. The direct water (medium) focusing and bubble formation is used in surgical and dental applications of lasers, where short, focused pulses and the resulting shock waves may be used to ablate material. Such techniques have also been used with cells in media, as described in "Sonoporation of suspension cells with a single cavitation bubble in a microfluidic confinement", Le Gac et al., Lab Chip, 2007, 7:1666-1672, herein incorporated by reference.

Figure 4:
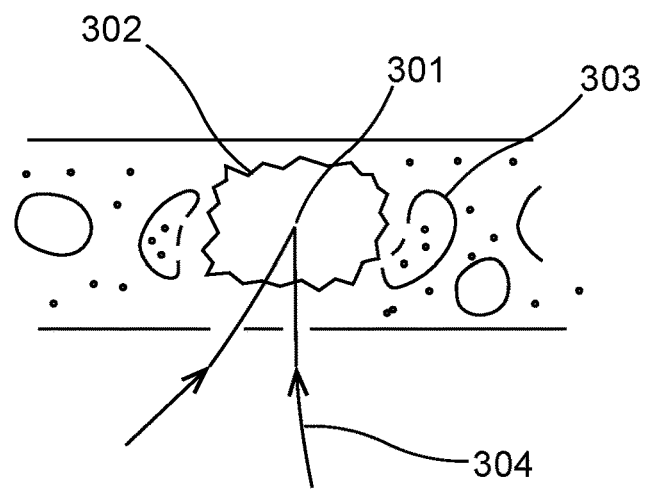
FIG. 4 shows a system where a laser beam is focused to a small volume for plasma and bubble formation.

FIG. 4 shows a simplified representation where a confined liquid environment such as a microfluidic cell is used to contain cells and cargo molecules. A laser beam 304 is focused to a small volume 301 to reach the required fluence and power for plasma and bubble 302 formation. The shock wave from the bubble expansion and collapse increases membrane permeability in nearby cells 303. The method suffers from a number of drawbacks: a large amount of power and energy is required to form bubbles, and therefore only a small volume may be addressed at a time, limiting system throughput (or requiring very powerful lasers); the very high fluence of the laser near the focus will directly damage or destroy any cells that are in the optical path; the effect on cells is highly variable depending on the distance from the focus point: close to the point, the cells will be destroyed by optical or plasma effects; at middle distance membrane permeability may be enhanced; at further distance there is no effect.

Features relating to combining conventional ultrasonic bubble generation and a laser pulse to control the collapse of a bubble may be used in embodiments of the present invention, such as described in "Controlled permeation of cell membrane by single bubble acoustic cavitation", Zhou et al, J. Controlled Release, 2011, 157(1):103-111, herein incorporated in its entirety by reference.

Figure 5:
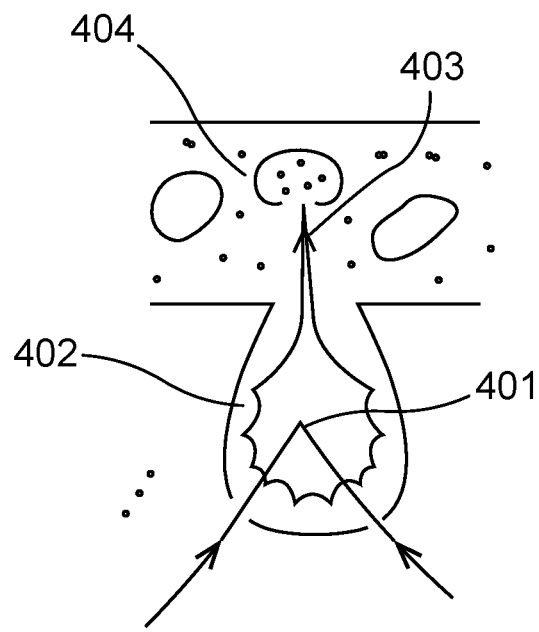
FIG. 5 shows a method for cell applications that uses a separate cavity where a laser is focused in order to cause bubble formation and a shockwave that projects a shockwave into a chamber with cells.

FIG. 5 shows another method that has been developed for cell applications. This method has uses a separate cavity 402 where the laser is focused 401 in order to cause bubble formation and a shockwave that projects a shockwave 403 into a chamber with cells 404. This layout has been used to redirect cells in a flow system, such as described in "Pulsed laser triggered high speed microfluidic fluorescence activated cell sorter", Wu et al, Lab Chip, 2012, 12(7):1378-1383, herein incorporated by reference. Such a configuration can only address a relatively small volume with a large amount of laser power, but does separate the laser focus from the cell-carrying volume, reducing the possibility of direct laser damage to the cells.

One potential approach to addressing larger volumes of cells using direct focusing in liquid medium is the use of diffractive optics or other techniques to onto multiple focused points in the liquid at once. Such a technique is described, for example, in "Generation of laser-induced cavitation bubbles with a digital hologram", Quinto-Su et al, Optics Express, 2008, 16(23):18964-18969, herein incorporated by reference. Using the technique, an array of bubbles may be formed in a liquid. However, when using the technique, cells directly in the laser focus points may be damaged or destroyed.

An alternative which does not put cells in the direct path of the illuminating lasers, and potentially a more even pressure wave across multiple cells, is to illuminate a target which itself experiences explosive effects as a result of intense laser radiation, and in turn transmits a pressure wave into adjacent liquid. This method has been used by many groups, often with sheets of highly-absorbing material (such as black rubber) that are destructively illuminated with pulsed lasers. The rubber sheet also functions as the pressure transducer to the liquid. Examples where this method has been used to apply pressure waves to cells include "Cell Loading with Laser-Generated Stress Waves: The Role of Stress Gradient", Mulholland et al, Pharmaceutical Research, 1999, 16(4):514-518, and "Efficient delivery of small interfering RNA to plant cells by a nanosecond pulsed laser-induced stress wave for posttranscriptional gene silencing", Tang et el, Plant Science, 2006, 171(3):375-381, which are hereby incorporated by reference. This method has been shown effective in producing pressure waves and permeating (or breaking) cell membranes. It functions by creating large-scale pressure waves, however, and it is often desirable to apply intense pressure on a small scale (even relative to a cell) to cause targeted permeation of the cell membrane.

One approach that has a significant history is the use of light-absorbing particles for the purpose of absorbing pulsed laser light and forming transient bubbles to either promote delivery of cargos through cell membranes, or to kill cells entirely by destroying their membranes. Typically metallic or other conductive nanoparticles are used to absorb light, as is described in the following examples, "Radiation and nanoparticles for enhancement of drug delivery in solid tumors, Rinat O. Esenaliev, U.S. Pat. No. 6,165,440; "Selective Cell Targeting with Light-Absorbing Microparticles and Nanoparticles", Pitsillides et al, Biophys. J., 2003, 84(6): 4023-4032; and "Delivery of molecules into cells using carbon nanoparticles activated by femtosecond laser pulses", Chakravarty et al, Nat. Nanotechnol., 2010, 5(8): 607-611, which are herein incorporated by reference.

Figure 6:
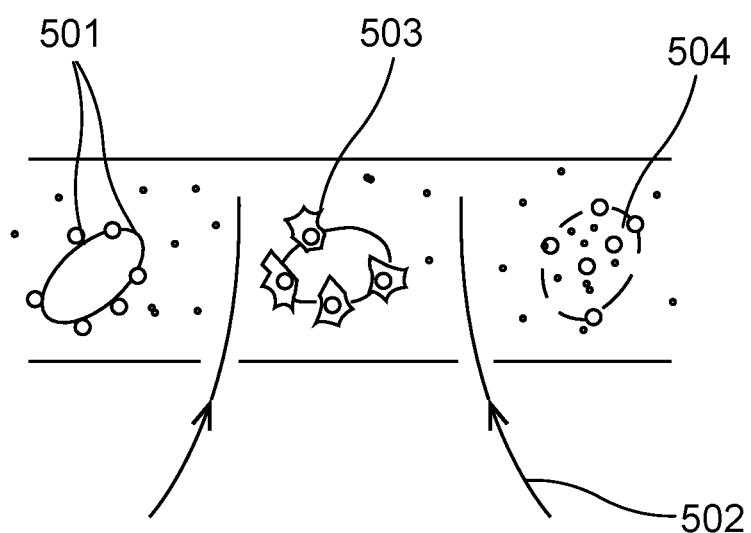
FIG. 6 shows a schematic of a method where nanoparticles may be free-floating in the cell medium, or attached to cells, as shown in this example. A pulsed laser beam illuminates the medium with cells and absorbing nanoparticles.

FIG. 6 shows a representative schematic of a method using nanoparticles 501, which may be free-floating in the cell medium, or attached to cells, as shown in this example. A pulsed laser beam 502 illuminates the medium with cells and absorbing nanoparticles. Note that unlike the direct liquid plasma formation, a less focused beam may be used, because the absorption of the nanoparticles is significantly higher than that of the liquid medium. The nanoparticles absorb the pulsed radiation, causing a rapid local temperature escalation and explosive bubble formation 503, at least some of which is close to the cell membrane; this in turn causes permeability (or directly opens pores) in the membrane, allowing a molecular cargo contained in the medium to enter the cell, as shown by 504. One significant concern with this method is the residual nanoparticles (or fragments of nanoparticles) that remain in the cells and cell medium. These may alter cell function, and possible cause mutations or other undesirable effects. This is a drawback in discovery applications, but even of greater concern where the cells will subsequently be used in patients, such as in gene therapy applications.

Formats where absorbers are permanently attached to substrates have been explored as mechanisms for transient bubble generation as well. Examples include "Super-Heating and Micro-Bubble Generation around Plasmonic Nanoparticles under cw Illumination", Baffou et al, J. Phys. Chem. C, 2014, 118(9):4890-4898; and "Formation and dissolution of microbubbles on highly-ordered plasmonic nanopillar arrays", Liu et al., Sci. Rep., 2015, 5, 18515, which are hereby incorporated by reference. Liu et al. also shows the impact of surface hydrophobicity or hydrophilicity on ultimate bubble duration (where hydrophilic surfaces will cause more rapid bubble collapse, as might be expected), and also the role of dissolved gases in the liquid, confirming some results in the first paper that showed metal nanoparticles that could create bubbles with lifetimes on the order of minutes.

Consistently fabricating a surface with spaces nano-absorbers such as gold spheres or gold pillars can be difficult, and the resulting surfaces may be very sensitive to mechanical or other wear.

Another approach to forming bubbles through the use of laser pulses is to use a sheet of absorbing material, patterned on a rigid surface, and in contact with the liquid medium. Two examples of this format, with first using a Chromium layer as an absorber, and the second using an amorphous silicon layer as an absorber, are "Transient Temperature During the Vaporization of Liquid on a Pulsed Laser-Heated Solid Surface", Park et al, J. Heat Transfer, 1996, 118(3): 702-708; and "Laser-induced microbubble poration of localized single cells", Fan et al, Lab Chip, 2014, 14, 1572, which are hereby incorporated by reference. Note that this method still requires relatively concentrated laser radiation in order to form bubbles, particularly if the surface is smooth and does not promote bubble nucleation. The second reference uses a design where the absorber/bubble forming layer is on the opposite surface of a microfluidic cavity from a surface on which cells are cultured, attached, or resting.

Features directed to porating cell membranes using lasers as a direct poration method may be used in certain embodiments of the invention. For example, the laser may be focused on the cell membrane and directly disrupt the cell membrane through thermal and/or bubble expansion means, such as described in "Femtosecond optical transfection of cells: viability and efficiency", Stevenson et al, Opt. Express, 2006, 14(16):7125-7133, and "Fast targeted gene transfection and optogenetic modification of single neurons using femtosecond laser irradiation", Antkowiak et al, Sci. Rep., 2013, 3, 3281, which are hereby incorporated by reference. The advantage of this approach is high precision, which allows even specific parts of cell membranes to be porated for the purpose of introducing molecular cargos or other constructs. A disadvantage is that throughput it very low and the technique suffers from the same issues as other direct-focus laser techniques, including potential cytotoxicity from ultra-high laser power (two-photon effects, thermal effects, etc).

Features relating to a "nanosubstrate" designed to absorb transient radiation, convert it to heat, and promote rapid bubble formation within a liquid medium for the purpose of porating membranes of proximate cells may be used in embodiments of the present invention, thereby allowing delivery of large cargos into these cells, or conversely extraction of large cargos from the cells. For example, substrates may have features that promote radiation absorption, energy concentration, and/or bubble nucleation, and are fabricated using very low-cost soft lithography techniques, as described in "Plasmonic Tipless Pyramids for Cell Poration", Courvoisier et al, Nano Lett., 2015, 15(7):4461-4466; "Intracellular delivery using nanosecond-laser excitation of large-area plasmonic substrates", Saklayen et al, ACS Nano, 2017, 11(4):3671-3680; Dynamics of transient microbubbles generated by fs-laser irradiation of plasmonic micropyramids, Chen et al, Appl. Phys. Lett., 2017, 110, 153102: "Plasmonic Nanocavity-Based Cell Therapy Method and System", Mazur et al, WIPO Patent Publication No. WO/2016/127069; and "Method and system for manipulation of cells", Mazur et al, US Patent Publication No. US 2012-0171746 A1 (2009), which are incorporated by reference herein.

Figure 7:
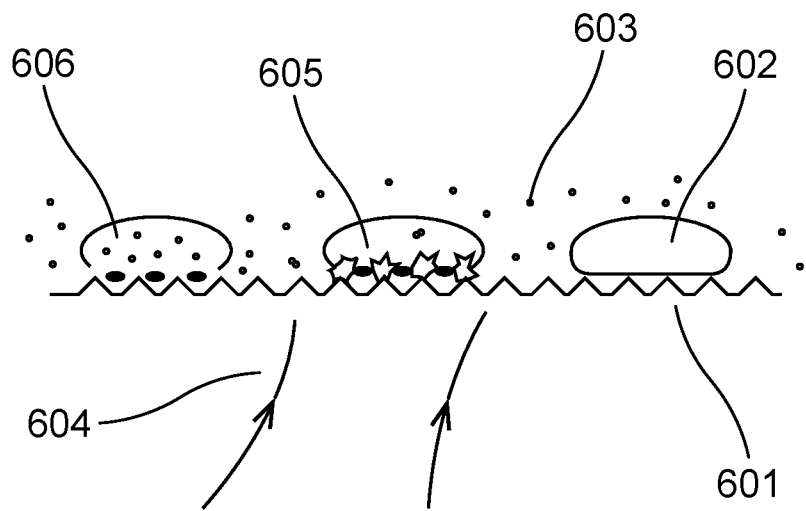
FIG. 7 shows a system where a substrate has a surface formed with small structures that promote bubble nucleation at specific sites (tops of pyramids, in this example), and is coated with a material that absorbs incoming laser radiation.

FIG. 7 shows a system where a substrate 601 has a surface formed with small structures that promote bubble nucleation at specific sites (tops of pyramids, in this example), and is coated with a material that absorbs incoming laser radiation. The substrate may be illuminated from top or bottom. Cells 602 rest on the surface, and cell medium 603 carries the cargo to be delivered to the cells. A beam 604 is used to illuminate the substrate in a pulsed manner, with femtosecond, picosecond, or nanosecond pulse duration. The short laser pulse causes transient local heating at the surface features, causing rapid bubble expansion and the contraction, and poration of the cell membrane 605. Subsequently, the cargo in the cell medium diffuses into the porated cell 606.

Pairing patterned radiation absorbers with "membrane" structures that enhance cargo delivery to cells may be used in certain embodiments. The format is an attempt to parallelize a delivery needle-tip format that included laser-driven vapor bubbles for cell membrane permeation. The parallel format is described in "Massively parallel delivery of large cargo into mammalian cells with light pulses", Wu et al, Nat. Methods, 2015, 12(5):439-444, which is incorporated by reference.

Figure 8:
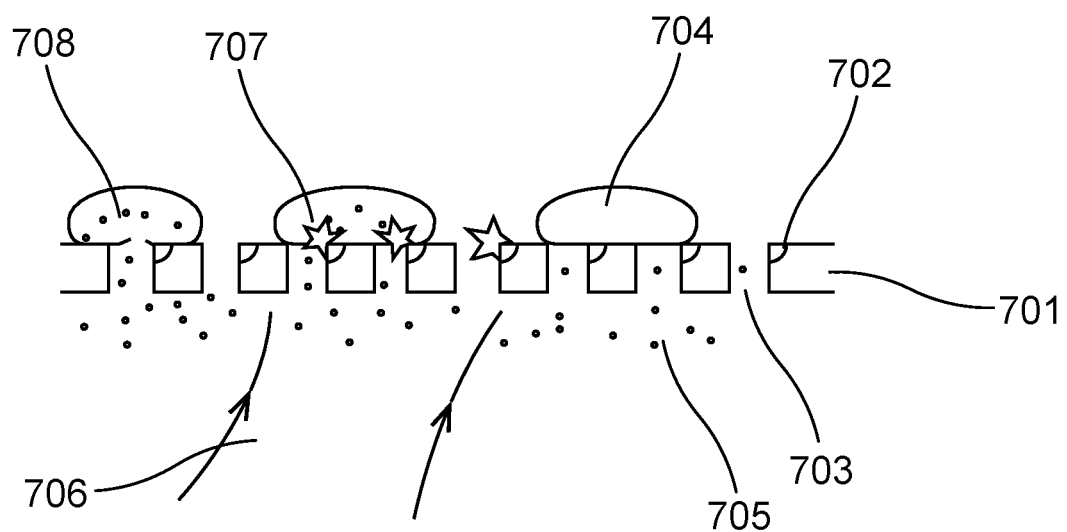
FIG. 8 shows a schematic of a method where a substrate with holes between a cargo reservoir and a cavity containing a cell medium has patterned absorbers that absorb pulsed laser radiation.

FIG. 8 shows a schematic of a method with a substrate 701 having holes 703 between a cargo reservoir 705 and a cavity containing cells 704 and cell medium has patterned absorbers 702 that absorb pulsed laser radiation 706, which causes cavitation bubbles to form and porate the cell membrane as in 707. Pressure is then applied to the cargo reservoir, and it enters the porated cells as shown in 708. An advantage of such a structure is the ability to better control delivery of cargo to the cells using a pressure differential—although this is clearly very limited by the need to maintain cell attachment to the surface. However, a disadvantage of such a system is that the structure is relatively complex to fabricate (multiple patterning and etch steps), the metallic conductor is applied in a non-standard way that may not be reproducible or consistent. The reservoir and pumping/ pressure system add additional complexity in return for the delivery capability described above. Another potential disadvantage of such a system is that the delivery of laser light is necessarily through the cell medium and cells themselves. This can result in inconsistent energy delivery, and exposes cells to high-intensity radiation.

Surface films used in all embodiments of the substrates in the present invention may include transparent conductive oxides that have been optimized for providing surface roughness in amorphous silicon solars cells. They may also include polymer, semiconductor or oxide films that have been roughened by exposure to chemical plasmas, or chemical etches employing pulsed lasers.

In some embodiments of the present invention, it may be desirable to isolate the molecular cargo to be delivered to cells and deliver it locally rather than through the general cell medium. In such cases, a layer on the substrate may be used to contain the cargo until just before, during, or after laser-activated bubble poration of the cells proximate to the substrate. One of a number of materials engineered for impregnation and controlled release of molecular cargos may be used. An example of such layers is described in "Near-infrared-actuated devices for remotely controlled drug delivery", Timko, Langer et al, PNAS, 2014, 111(4): 1349-1354, which is hereby incorporated by reference. The release of the cargo into the space between the cells and the surface may be achieved in a number of ways: simple diffusion, by which the molecular cargo diffuses into the space between the cell and substrate over some time before laser activation, with the rate of this diffusion controlled by the properties (porosity, etc) of the materials; thermal means, where the layer is heated to release its contents (for example by a laser, which may or may not be the same laser that causes bubble nucleation); or other means including but not limited to optical, magnetic and electrical. In this manner, a cargo may be preloaded into the functional substrate, and released only when delivery into the cell (due to bubble permeation) is possible. This minimizes the cargo required, and places it precisely where it is required for intracellular delivery.

Whereas prior work on patterned substrate plus laser-activated bubble nucleation for intracellular transfection was done using cells that were either cultured on the laser-addressed substrate, or centrifuged to temporarily adhere to the surface, there are cases where it may be desirable to process cells that are proximate to, but not in contact with, the laser-addressed surfaces described above.

In particular, it may be desirable to process cells in a format where the cells may flow in and out of the volume being processed with laser pulses and bubble shockwaves, rather than batch processed on a substrate such as a well plate or culture flask.

Figure 9:
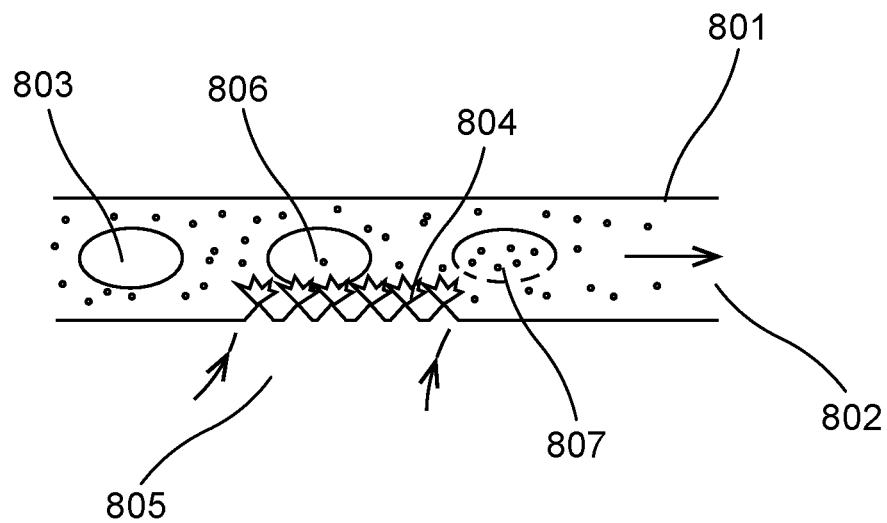
FIG. 9 shows an embodiment of a microfluidic-based intracellular delivery system.

FIG. 9 shows an example embodiment of a microfluidic-based intracellular delivery system in the invention. A side view of a fluid channel 801 is shown. The channel carries a flow of liquid 802 which includes cells 803, cell medium, and cargo molecules (that will be inserted into cells using the present method). The flow 802 may either be continuous, or a "stopped" flow where material is transported, stopped temporarily for processing in the active region, and then transported out of the active region. One or more laser pulses 805 is used to illuminate the active region 804 which may include absorbing and/or bubble nucleating elements as described herein, causing explosive bubble formation and pressure waves in a consistent pattern across the active region, and porating the membranes of cells passing through it 806. Cells with temporarily permeated membrane 807 then take up the molecular cargo in the flow, completing the delivery process, and then are transported out of the device in the flow 802.

In an embodiment, the flow consists of a single flow carrying cells, cell medium and molecular cargo—all of which is pushed through a narrow channel (relative to cell dimension) to ensure cell membranes pass close to the active bubble-forming surface. In this simple format, the invention resembles the "cell squeezing" methods described above and depicted by FIG. 2 or FIG. 3, with the critical difference being that there is no fixed obstruction in the fluid channel, and force on the cell is not dependent on high-velocity transport through this obstruction. Instead, the pressure is caused by laser-activated explosive bubble formation as the cells pass through the constriction-free channel.

As such, the present invention has several significant, non-limited advantages over the prior art. In particular, the present invention does not have a narrow constriction prone to clogging. The present invention does not require extreme pressure or flow velocities, which may result in shear damage to cells. Further, the present invention provides a high degree of flexibility by use of laser pulse power, laser pulse timing, and laser spatial focusing that are absent in a mechanically-defined "squeezing" design.

In other embodiments of the flow design, the flow through the active (laser-addressed) region is formed from multiple flows that are combined in a laminar fashion, using fluidic techniques and constructs that are well-known in the industry. See for example "Universally applicable three-dimensional hydrodynamic microfluidic flow focusing", Chiu et al, Lab Chip, 2013, 13(9):1803-1809, which is hereby incorporated by reference. In the present invention, two or more flows may be combined to "set" the vertical position of the cells in the flow channel, thereby fixing the distance from the bubble surface to the cell membrane, and allowing repeatable impulses from the laser-activated bubbles to the cell membrane.

For example, three flow layers could be combined vertically, a thin bottom (sheath) layer that ultimately establishes spacing between the cells and the active surface, a thin layer carrying cells (in a "monolayer"), and a top sheath layer that provides a buffer from the top of the channel. This design allows a relatively tall channel with very little clogging potential, and maintains a fixed spacing between the laser-activated surface and the bottom cell membranes.

A full 3-dimensional focusing system could additionally center the cells in the channel horizontally, if so desired, to get highly uniform shockwave treatment for the cells as they pass through the active area with pulsed laser illumination.

Figure 10:
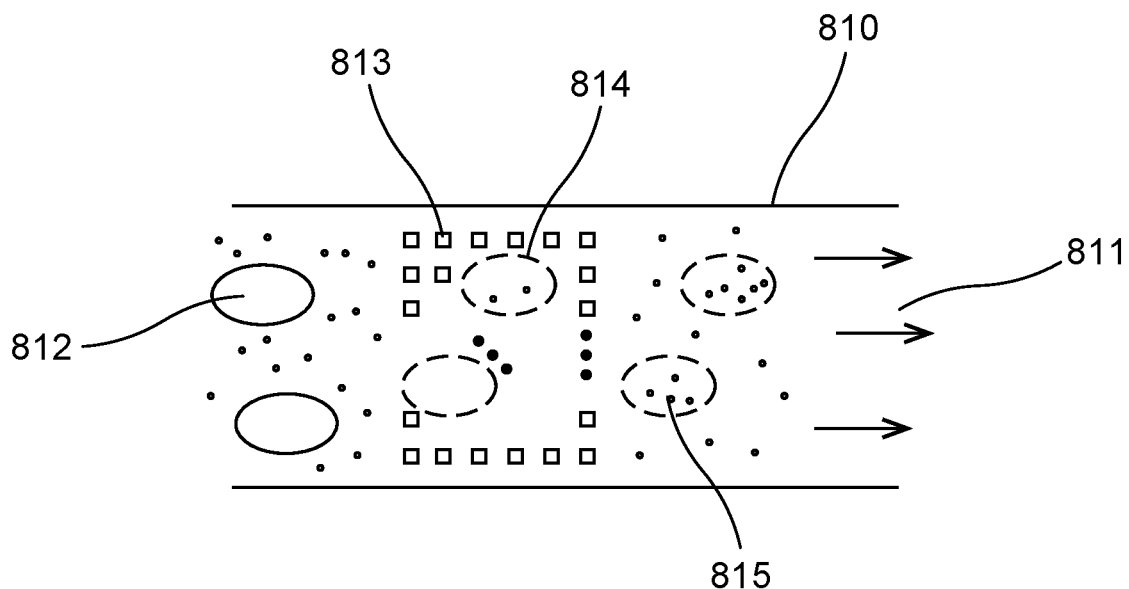
FIG. 10 shows a top view of a channel in an example embodiment in a format where a flow in a relatively wide channel is used.

FIG. 10 shows an example top view of the fluid channel described in FIG. 9, in a format where a flow 811 in a relatively wide channel 810 is used (where multiple cells 812 may pass through a cross-section simultaneously to enhance capacity and reduce clogging risk). In this embodiment, the active area is patterned with features 813 that absorb pulsed laser radiation and act as nucleation points for bubbles, thus providing a consistent array of pressure waves to permeate the membranes of cells 814 passing through the active area. The temporarily membrane-permeated cells 815 then take up the molecular cargo from the surrounding medium.

Figure 11:
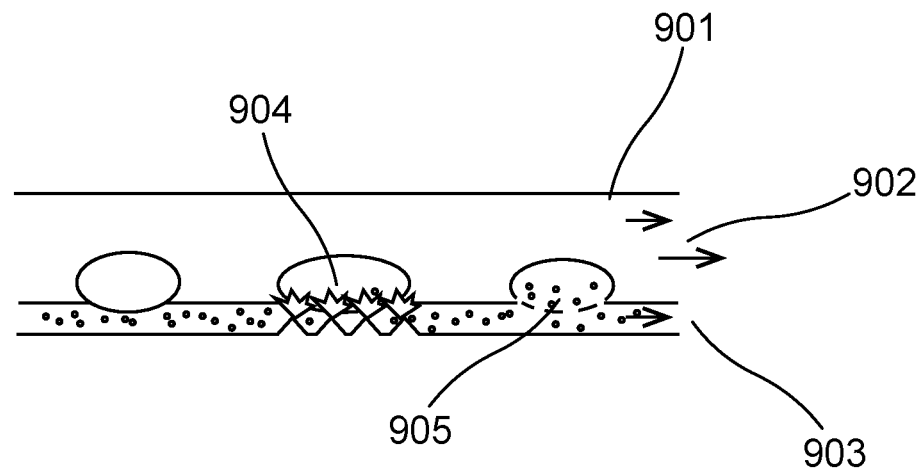
FIG. 11 shows an embodiment of the invention where a microfluidic channel has upstream features (not shown) to create a multi-layer laminar flow.

FIG. 11 depicts another embodiment of the present invention. In this embodiment, a microfluidic channel 901 has upstream features (not shown) to create a multi-layer laminar flow, as described above and using methods and constructs well known in the industry. One of the flow layers 903, namely the one that separates the cell flow from the active surface, contains the molecular cargo to be delivered to the cells. As the cells move through the active area, transient bubbles (activated by laser pulses) are formed to permeate the membrane, as well as push the cargo-bearing medium towards the permeated cell 904. As cells flow out of the active region (and as their membranes repair, usually over the course of seconds) the cargo diffuses from the cargo-bearing layer into the cells as shown by 905. In this manner, a minimum amount of cargo molecule is used, and is placed precisely where it can be delivered most efficiently into the cell.

Figure 12:
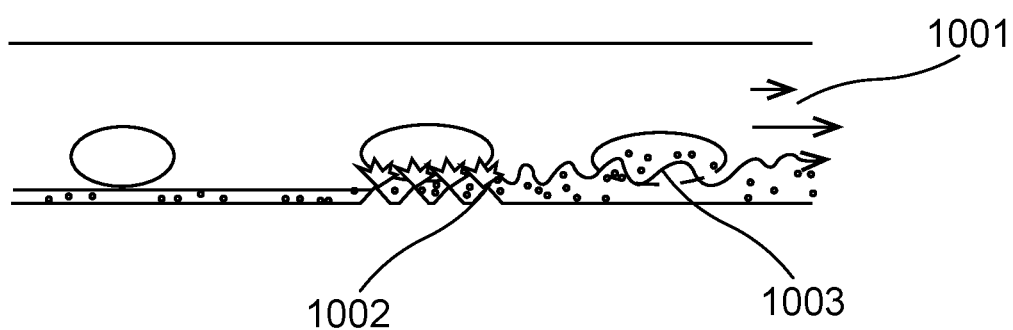
FIG. 12 shows an embodiment of the invention with a stratified flow where the molecular cargo is isolated next to the cell flow.

A similar embodiment is shown in FIG. 12, again with a stratified flow where the molecular cargo is isolated next to the cell flow. Here, the active area, or a region just upstream or downstream of the active area ("active area" is used herein to mean the region where laser-induced bubbles permeate cell membranes) contains features 1002 designed to induce fluctuations or turbulence in the flow 1001, disrupting the interface between the cell-carrying flow and cargo-carrying flow for the purpose of promoting delivery of the molecular cargos into the cell 1003. These features may be the same features used to form the laser-activated bubbles, or additional, purpose-built features.

Other methods and constructs may be used to promote delivery of the molecular cargo into the cell within the present invention. Some such as the turbulence-based approach described above are applicable to flow-based systems, while others can be used in either flow or stationary systems where the cells are stationary or even attached to the substrate.

For example, thermal means may be used before, during, or after laser-activated bubble poration to increase diffusion of the cargo towards the cell membrane, and then into the cell once it has been porated. For example, heating can be applied to the active face of the device to increase diffusion of large molecules away from the surface. This heating may be done electrically, or optically, for example with a laser (which may be the same laser used to form bubbles, or a different laser) or lamp that is applied throughout the delivery cycle. Using appropriately selected laser powers, wavelengths, and materials, a temperature profile in the medium and therefore molecular diffusion could be set up to optimize cargo delivery into target cells.

Thermal effects may be used in addition to promote membrane opening during the laser-activated bubble process. For example, low-power laser pulses or continuous wave radiation may heat the substrate surface and/or structures formed on it in order to gently heat the cell membranes above it. Then upon pulsed laser formation of the bubbles on the surface, the cell membrane is predisposed to be permeated by the resulting pressure waves.

An electric field may also be applied to promote movement of cargo into the cell, in particular where the cargo molecules/constructs have a net charge. In some cases, the same features that are used to generate porating bubbles may be used to generate local electric fields. For example, if gold-coated pyramid structures are used, a voltage could be applied to the entire layer, and to the opposite face of the fluid channel/manifold, generating intense electric fields near the pyramid tips that could be used to drive cargo molecules into the cells. In other embodiments, alternating rows or elements of these features could have positive or negative relative voltages applied to them, generating local fields to promote cargo transport.

In other embodiments, additional bubbles or cavitation effects may be used to promote cargo delivery. These bubbles could be formed by another (or the same) laser pulse process, the effect of which would be to force some of the cargo molecule into the porated cells.

In other embodiments, ultrasonic transducer means may be used to temporarily increase diffusion rates of molecules, in order to maximize delivery of cargo into target cells. The ultrasonic transducer may be used in addition to promote bubble nucleation that is triggered by the laser. In other words, the ultrasound mechanism "primes" the system for cavitation, and the laser delivers the trigger in order to get highly-repeatable, spatially-controlled bubbles/cavitation for the purpose of porating cells.

In other embodiments, cell media incorporating compounds that specifically inhibit and/or promote cell membrane re-sealing may be used in the present invention. For example, for particularly sensitive cells, compounds promoting re-sealing may be introduced before bubble delivery. For other cells, chemicals preventing sealing may be added, and then washed away at some time after bubble-based deliver of cargo.

These methods are applicable to both systems where cargo is generally present in the cell medium, and to embodiments where the cargo is relatively isolated to a layer (a liquid layer as described in some of the flow embodiments, or a permeable layer with controlled release as described above).

Figure 13:
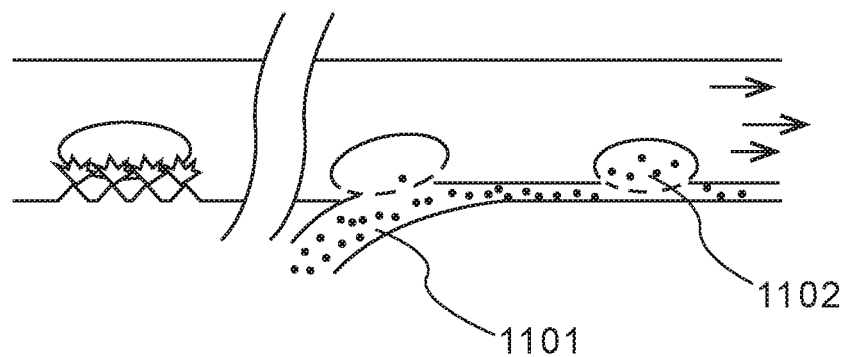
FIG. 13 shows an embodiment of the invention where a separate cargo-carrying flow is merged with the cell flow subsequent to laser-bubble poration.

FIG. 13 shows an embodiment of the present invention where a separate cargo-carrying flow 1101 is merged with the cell flow subsequent to laser-bubble poration, enabling cargo uptake 1102 in a controlled region, and again with small amounts of cargo delivered efficiently to the cell.

Figure 14:
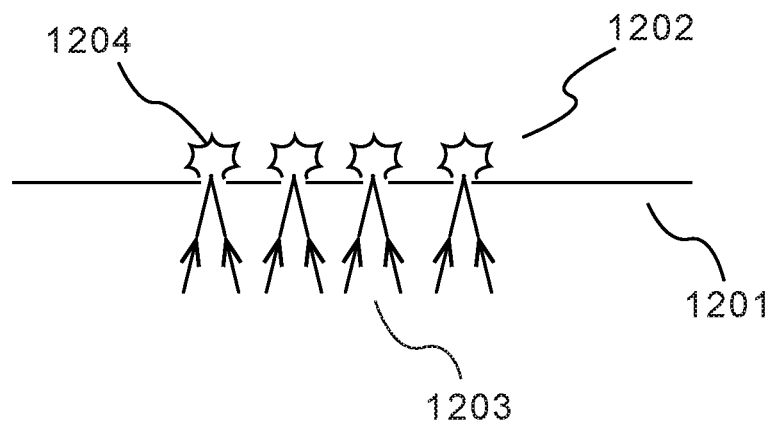
FIG. 14 depicts an embodiment of the surface or substrate in the present invention.

FIG. 14 depicts one embodiment of the surface used in the present invention. In this embodiment a surface 1201, substantially transparent to the pulsed laser radiation 1203 is adjacent to the cell medium 1202 which will contain cells, cell medium, and potentially cargo-carrying solution (the cell medium and cargo-carrying solution may be the same, or different, as described herein). In this embodiment, the pulsed laser radiation is focused onto one or more points at the interface between the substrate and liquid. The proposed design is as follows: to focus the radiation at the interface to promote bubble nucleation at significantly lower energies than are achieved when light is focused in the liquid medium. Besides being advantageous from an energy/laser power standpoint, it also localizes bubble formation near the solid substrate, which will maximize the shockwave into the medium. Specifically, two additional design factors may be used to achieve this: use of a wavelength (or wavelengths) that are highly absorbed in the liquid medium.

For example, such a system (and other embodiments described herein) could use a laser emitting at approximately 3 microns, such as an Er:YAG laser (2940 nm emission), where water has extremely high absorption. As a result, all optical energy is absorbed in a very shallow layer of water (~1 micron), greatly concentrating the thermal effect, and isolating much of the cell body from optical interactions. Other wavelengths with high absorption in water include (but are not limited to) ~1.5 µm, 2.0 µm, and >10 µm (where relatively low-cost, high-power $CO_2$ lasers emit).

Additionally, the surface of the substrate 1201 may be made of a material that promotes bubble nucleation, or be pre-treated in order to catalyze bubble nucleation, by chemical, physical and/or optical means (for example, a chemical etch, or chemical-laser etch that roughens the surface at a nanoscale to promote bubble nucleation).

As a result of illumination by a laser pulse, then, the surface produces regularly-spaced transient bubbles 1204 that cause pressure waves which in turn permeate cell substrates. Note that with sufficient local absorption and sufficiently good nucleation on the surface (as described above), a single relatively unfocused pulse could be used to illuminate a larger area and generate multiple bubbles, albeit in less predictable spacing than with the single or multiple focused spots.

The present invention, however, has significant advantages over prior systems using visible or NIR (1064 nm) pulsed lasers focused at spots inside the liquid. It has the potential to create bubbles over a larger area and/or with less laser power, and prevent direct damage to cells in the medium by focusing the radiation at the interface, and using wavelengths that are strongly absorbed by water.

Figure 15:
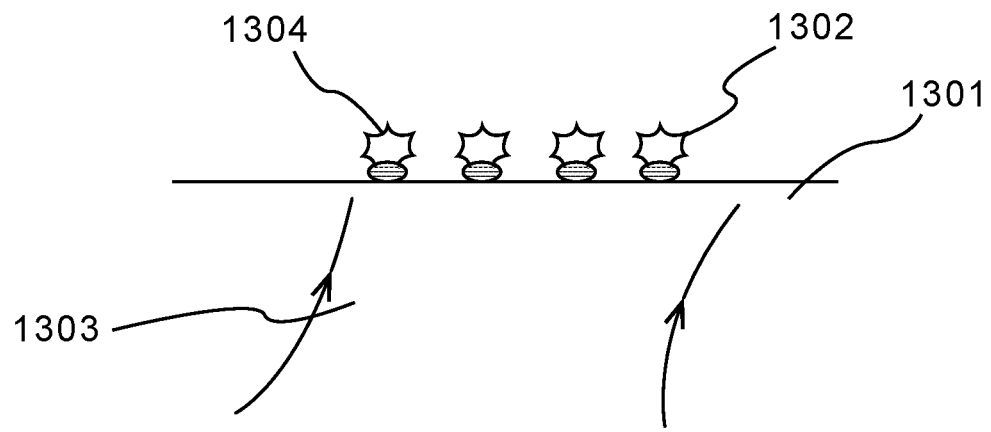
FIG. 15 depicts an embodiment of the surface or substrate in the invention.

FIG. 15 depicts another embodiment of the substrates in the invention. A flat substrate 1301 is patterned with features 1302 which serve to absorb laser radiation and/or nucleate bubble formation 1304 in a pre-determined pattern when pulse-illuminated by laser source 1303. The features may be additive, as shown here, meaning they are a patterned layer of material, such as a thin layer of metal (Au, Ti, Cr, among others), polymer materials, ink-containing polymers (for the purpose of promoting absorption), or for example an oxide layer that strongly absorbs when a mid-infrared laser source is used (for example, $SiO_2$ that has been patterned on the surface by a selective etch process, and then exposed to $CO_2$ laser pulses). In another embodiment, these features could simply serve the purpose of promoting bubble nucleation at pre-determined sites. For example, a laser with a wavelength strongly absorbed by the liquid medium could be used, and the features could be patches of the substrate that have been roughened with chemical, plasma, optical or physical means to promote nucleation. In an example, the features could be patterned out of a material with surface characteristics that promotes nucleation. The net effect of any of these configurations is to allow a relatively large area to be addressed by a laser pulse, but to generate bubbles with a highly-repeatable spatial pattern.

Figure 16:
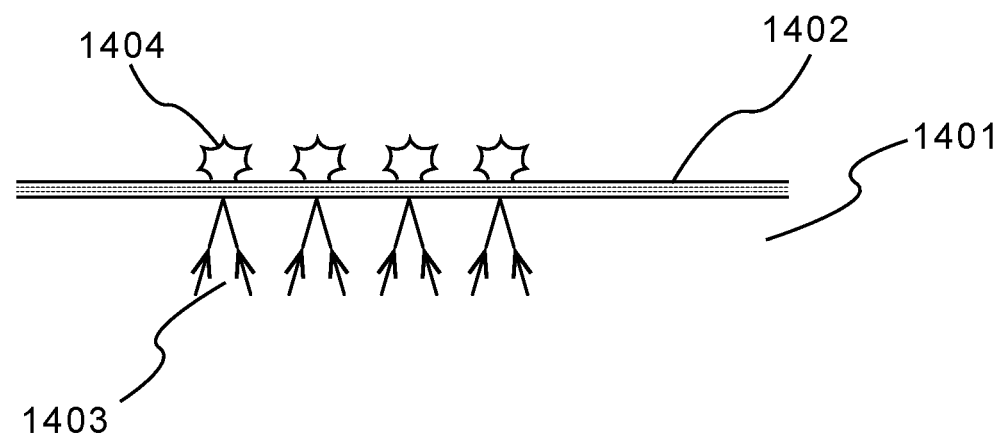
FIG. 16 depicts an embodiment of the surface or substrate in the invention.

FIG. 16 depicts another embodiment of the substrates in the present invention. A substrate 1401 is coated with a continuous layer 1402 which serves to absorb laser radiation and/or promote bubble nucleation. This layer may consist of (but not be limited to) metallic films, polymer films, oxide films, nitride films, and semiconductor films such as amorphous Silicon. In this embodiment, laser energy 1403 is focused on one or more points on the surface to determine where bubble nucleation 1404 occurs.

In any of the embodiments herein which involve focusing the laser on multiple points on the substrate, the point pattern may be fixed and set by the use of a diffractive optical element ahead of the focusing lens, or it may be generated by a spatial light modulator (SLM) in the Fourier plan ahead of the focusing lens. The use of an SLM allows for reconfiguration of the point pattern, to change the number of bubble points, spacing of bubble points, and shape of the bubble point pattern.

Figure 17:
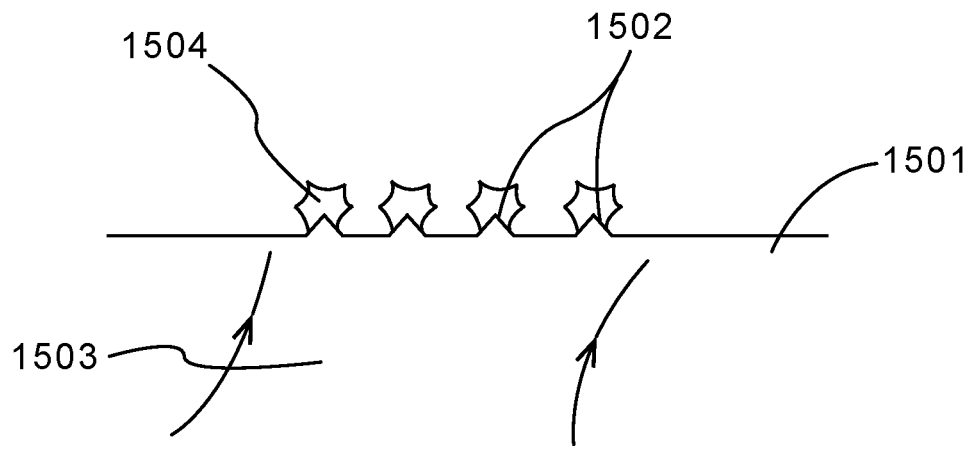
FIG. 17 depicts an embodiment of the surface in the present invention where a substrate is patterned with features that serve as nucleation points on the surface.

FIG. 17 depicts one embodiment of the surfaces in the present invention where a substrate 1501 is patterned with features 1502 that serve as nucleation points on the surface, such that heating provided by laser pulse 1503 translates to bubble formation 1504 at pre-determined points. This configuration is suited for laser wavelengths that are strongly absorbed near the substrate-liquid interface, such as wavelengths that are strongly absorbed by water.

Figure 18:
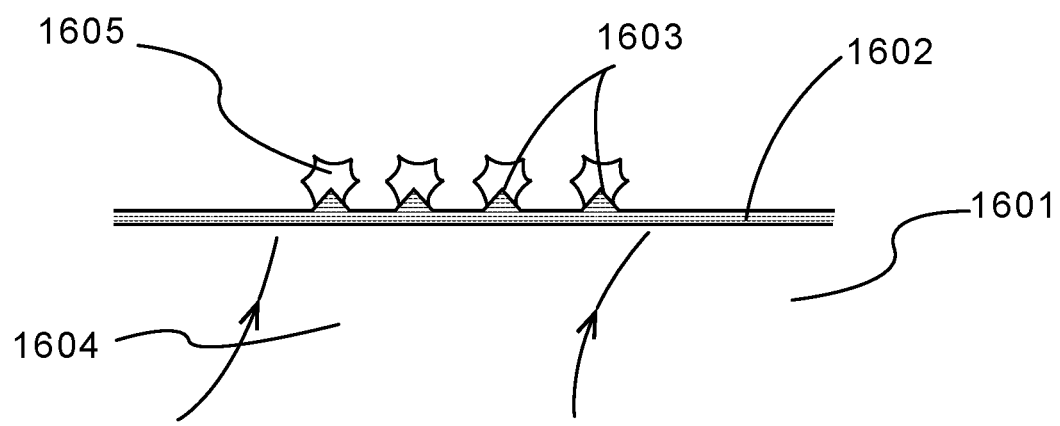
FIG. 18 depicts an embodiment of the surface.

FIG. 18 depicts one embodiment depicts one embodiment of the surfaces in the present invention where a substrate 1601 is coated with an absorbing material 1602 and also patterned with features 1603 to promote bubble nucleation 1605 in response to exposure to laser pulses 1604.

In certain embodiments, the invention further comprises adding contrast-agent type microbubbles to the liquid around the cell layer. Further, a first set of microbubbles may be laser-generated and then imploded by a second set of laser-generated bubbles. The addition of gas-filled layers or structures in proximity to the cells enhances the effect of the laser-activated bubbles, allowing the laser-activated surfaces to be further removed from the cells themselves, making the delivery more consistent over a range of conditions, and allowing further optimization of the mechanical conditions surrounding the cells. In some embodiments of the present invention, the supplementary gas bubbles may be coated with cargo molecules or constructs to be delivered into cells, and the optically-activated bubbles are used to completely disrupt/collapse the supplementary bubbles, and potentially create liquid jetting, upon which the attached cargos diffuse through or are jet-delivered through the cell membranes.

Figure 19:
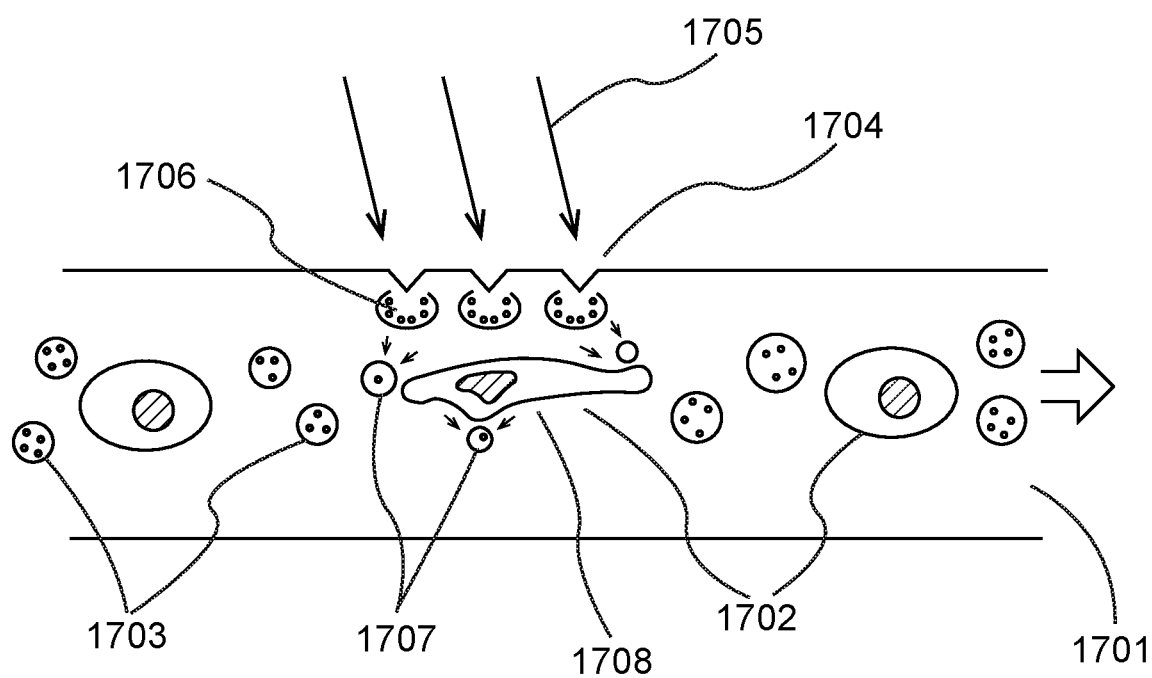
FIG. 19 shows an embodiment of the present invention in which gas-filled microbubbles contained in the same core flow, and in close proximity to cells, within a microfluidic flow or stopped-flow chamber, are used as an elastic interface to enable motion and stretching in cells.

FIG. 19 depicts an embodiment of the present invention in which gas-filled microbubbles contained in the same core flow, and in close proximity to cells, within a microfluidic flow or stopped-flow chamber, are used as an elastic interface to enable motion and stretching in cells. A microfluidic flow 1701 contains cells 1702 which flow from left to right in this depiction. Comingled with these cells are supplementary gas bubbles 1703. On at least one surface of the microfluidic flow chamber there is an active surface 1704. As optical energy pulses 1705 are deposited into the active surface, it causes transient microbubbles 1706 to form inside the microfluidic chamber. The expansion and collapse of these bubbles cause pressure waves within the fluid flow, which in turn causes the supplementary bubbles to contract and expand as depicted by 1707. This expansion and contraction in close proximity to the cells create strain on the cell membranes as indicated by 1708, increasing cell membrane permeability, and allowing cargo to diffuse into or out of the cells.

The fluid flow may be within a channel where cells and supplementary bubbles are confined to roughly a 1-dimensional core flow as depicted above. Alternatively, the flow may form a 2-dimensional "sheet" where cells and supplementary bubbles flow in a sheet at the center of a 2-D channel. In another embodiment, the supplementary microbubbles may be confined to a separate layer adjacent to the cells, and combined in a laminar fashion before the microbubble delivery section depicted here. In one embodiment the supplementary microbubbles may flow in a layer between the active surface and cells; in this embodiment, sufficient energy may be delivered to the active surface to create pressure waves sufficient to completely collapse/explode the supplementary microbubbles, causing a large energy release and potentially liquid jetting into the cell layer.

Figure 20:
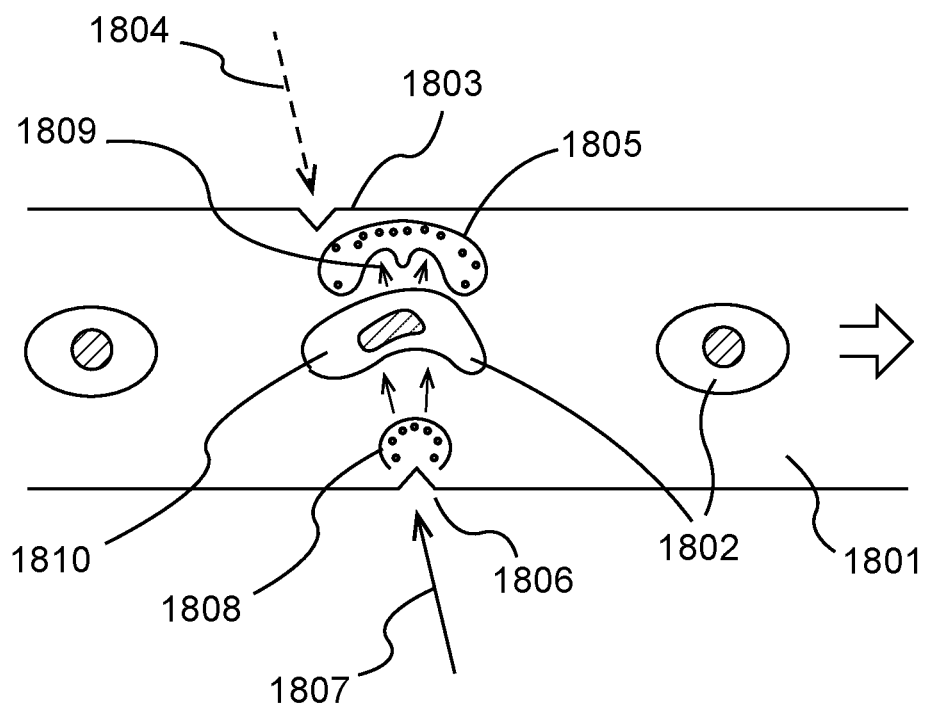
FIG. 20 shows an embodiment of the invention in which a first set of energy-induced transient microbubbles is rapidly collapsed by a second set of energy-induced transient microbubbles.

FIG. 20 depicts an embodiment of the present invention in which a first set of energy-induced transient microbubbles is rapidly collapsed by a second set of energy-induced transient microbubbles, causing rapid displacement and stretching of cell membranes, where the cells are in a flow or stopped-flow channel. A liquid channel 1801 contains a flow (to the right, in this example) with cells 1802, here shown in a core flow at a set distance from the walls of the channels. A first active surface or feature 1803 is pulse-illuminated with a first energy pulse 1804, resulting in the rapid nucleation and expansion of first transient microbubble(s) 1805. A second active surface or surface feature 1806 is illuminated by a second pulse 1807, forming second transient microbubble(s) 1808. Depending on the flow velocity and the desired relative timing between the first and second transient microbubbles, a physical displacement along the direction of the flow may be used, as shown in this example. The expansion of the second microbubble(s) and resulting pressure waves cause the rapid collapse of the first microbubble(s), as indicated by 1809. This collapse causes rapid displacement within the liquid and deformation of, and strain on, the cell membranes, as indicated by 1810. The resulting temporary permeability of the cell membrane may then be used to extract cargos, or insert cargos into the cell.

Various arrangements of flows are possible. For example, both 1-D focused and 2-D focused are possible. Further, an arrangement of flow in an embodiment comprises layered flows with cargo in separate layers from cells. In certain embodiments, rather than delivering cargo into cells, the present invention may be used to porate cells for the purpose of extracting certain large molecules or constructs from those cells. The present invention generally applies to this function as well, as it porates cell membranes in a manner that allow transport of materials in either direction.

Selective cell poration is applicable to the invention. Where cells are stationary on the laser-activated substrates, microscopy or other imaging may be used to select cells, or even portions of cells, to porate. As opposed to previous work, cited above, where cell membranes are directly disrupted by lasers (with potential phototoxic effects), the use of the substrate allows for a pressure-driven effect, but still allows localization of the effect for selective delivery to cells.

In flow-based systems, the present invention may be combined with known cytometry techniques (including but not limited to fluorescent flow cytometry, imaging cytometry, scattering cytometry, spectroscopic cytometry) to identify and selectively porate cells as they pass through the "active region" of the flow. In this case, laser pulses to activate bubbles are only used when the appropriate cell enters the active region.

In a more passive scenario, cells may be sorted/selected upstream from the active region, for example by mechanical or flow features that separate cells by size, shape, or buoyancy—or by active sorting mechanisms well known in the industry.

Figure 21:
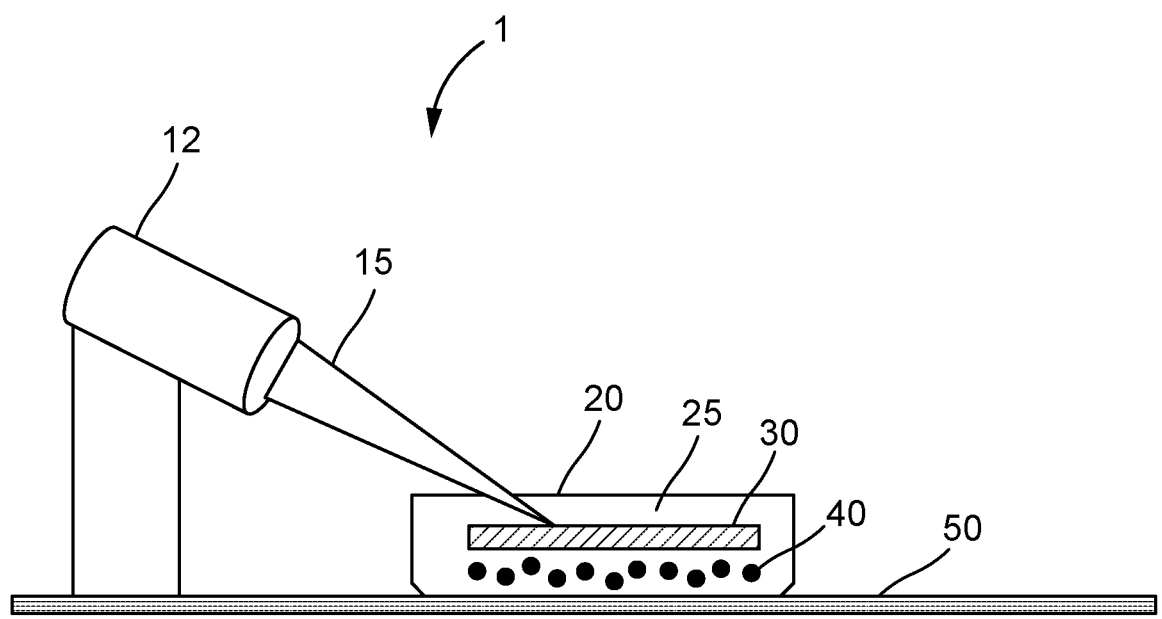
FIG. 21 shows a system according to the present invention.

FIG. 21 shows an embodiment of an intracellular delivery system 1 according to the present invention. The system 1 includes a light source or laser 12 that produces a laser pulse 15. The laser 12 may be attached to an instrument. For example, the laser 12 may be any suitable laser, such as a continuous wave laser sold under the trademark RED-POWER from SPI Lasers UK Limited (Southampton, United Kingdom). The laser pulse 15 is directed at a laser-activated surface 30. The laser pulse 15 is translated from optical energy into mechanical energy in the form of a pressure wave. The laser-activated surface 30 may be in a container 20. The container 20 may be any suitable container, such as a chip, microfluidic chip, cuvette dish, sample dish, or petri dish. The container 20 also contains cells 40 and a cargo-containing liquid or medium 25. The cells 40 are positioned at a distance from the laser-activated surface 30. The cells 40 may be continuously flowing or stationary in the cargo-containing medium or liquid that surrounds the cells. The laser pulse 15 permeates membranes of the cells 40 to deliver or extract cargo from the cells into a liquid surrounding the cells 40. The system 1 may be arranged on any suitable workspace, such as a workstation 50 in a research laboratory.

The present invention makes use of laser pulses to promote nucleation, growth, and collapse of bubbles on a surface facing cell membranes. A variety of optical sources, or lasers, may be used, including but not limited to diode- or lamp-pumped solid state lasers, gas lasers, fiber lasers, diode lasers, and quantum cascade lasers. Radiation pulses durations may be in the range of 10-100 fs, 100-1000 fs, 1-10 ps, 10-100 ps, 100-1000 ps, 1-10 ns, 1-100 ns, 100-1000 ns, 1-10 μs, or 10 μs-100 μs. The light source may be Q-switched, directly modulated, or chopped/redirected to produce these pulses. Additionally, a continuous wave (CW) laser may be used together with appropriate beam shaping and spatial scanning such that the illumination of any one area of the substrate effectively produces rapid pulses with durations as specified above.

The wavelength of the light source or laser may be in the UV, visible, NIR, mid-IR, or long wavelength IR ranges. The UV range has the advantage that beams can be very tightly focused and there is good absorption in a range of materials including some materials that are transparent in the visible regime (for microscopy). For example, a 355 nm wavelength may be used. The visible range has the advantage that there are a wide range of sources available, light can be focused tightly at the scale of cells, and system construction and safety is enhanced by having a directly visible emission. A 532 nm wavelength is a wavelength with good options for lasers (Nd:YAG) and accompanying optics specifically coated and designed for this wavelength. The NIR has the advantage that many high-energy pulsed sources for industrial, telecom and other applications are made in this range (1064 nm, and ~1500 nm, specifically). At ~1500 nm, there is relatively strong water absorption, which is helpful in certain designs as described above, and increases eye safety. Further, the mid-IR has the advantage that there is extremely high water absorption, which may allow for very simple substrate designs where the medium itself is the primary laser energy absorber. The long wavelength IR has the advantage that very high power, low cost sources ($CO_2$ lasers, at around 10.6 μm) are available, and water is a good absorber.

Any suitable molecular cargo may be delivered into or extracted from any suitable cell. The present invention may deliver molecular cargos into cell types that include, but are not limited to plant cells, animal cell, human cells, insect-derived cells, bacteria, adherent cells, suspension cells, cardiomyocytes, primary neurons, HeLa cells, stem cells, ESCs, iPSCs, hepatocytes, primary heart valve cells, gastrointestinal cells, k562s, lymphocytes, T-cells, Bcells, natural killer cells, dendritic cells, hematopeotic cells, beta cells, somatic cells, germ cells, embryos (human and animal), zygotes, gametes, 1205 Lu, 1321N1, 143B, 22Rv1, 23132/87, 293, 293 [suspension], 293-F cells sold under the trademark FREESTYLE by Thermo Fisher Scientific (Waltham, Mass.), 293T, 2A8, 2PK3, 300.19, 32D, 3A9, 3T3-L1 ad, 3T3-L1 pre-ad, 3T3-Swiss albino, 4T1, 5838 Ewing's, 661W, 697, 7-17, 720, 721.174, 721.22, 721.221, 786-0, A-10, A-375, A-431, A-498, A-673, A172, A2.A2, A20, A2058, A2780, A3.01, A549, A7r5, Adipocyte (pre), Adipocyte (pre)-human diabetes Tp.2, Adipose stem cell-human diabetes Tp.1, Adipose stem cell-human diabetes Tp.2, Adipose stem cell, Adrenocortical, AGN2a, AGS, AML, AML-DC, ARH 77, ARPE-19, arteries mesenteric (MA), astrocyte glioblastoma line-mouse, Astrocyte-human (NHA), Astrocyte-mouse, Astrocyte-rat, Astrocyte, ASZ001, AT-1, ATDC5, B cell-human, B-cell-lymphoma cell line, B-cell-mouse-stimulated, B-CLL, b-END, B157, B16-F0, B16-F1, B16-F10, B35, B3Z, B65, BA/F3, *Babesia Bovis*, Balb/c 3T3, BC-1, BCBL1, BCL1 clone 5B1b, BCL1.3B3, BE2-M17, BEAS-2B, Beta islet cell, BeWo, BHK-21, BHP2-7, BJ, BJ1-hTERT, BJAB, BJMC3879, BL2, BL3, BLCL, BPH1, BRIN-BD11, BT-20, BT549, BV173, BV2, BW5147, BW5147.3, BxPC-3, C10/MJ2, C17.2, C28A2, C2C12, C2F3, C3H10T1/2, C57MG, C6, C8161, CA46, Caco-2, Caco-2/TC7, Cal-1, Cal-85-1, CAL51, Calu-3, Calu-6, CAMA 1, CAP (CEVEC's Amniocyte Production), Capan-1, Capan2, Cardiomyocyte, CCD18Co, CCRF-CEM, CCRF-CEM C7, CD34+ cell, CEM-C7A, CEM.C1, Cervical stroma, CFBE, CH1, CH12, CH12F3, CH27, CHM 2100, CHO [suspension], CHO-DG44, CHO-DG44 (DHFR-), CHO-K1, CHO-S cells sold under the trademark FREESTYLE by Thermo Fisher Scientific (Waltham, Mass.), CHO-S [suspension], Chondrocyte (human (NHAC-kn)), Chondrocytes (mouse), Chromaffin cells (cow), CML, Colo201, Colo205, Colo357, Cor.At Cardiomyocytes (from ESC-mouse), COS-1, COS-7, CRFK, CTLL-2, CV1, Cytokine induced killer, Cytotrophoblast, D1 ORL UVA, D1F4, D283, D425, D54, Dante-BL, Daudi, DCIS, Dendritic cell (human), Dendritic cell (mouse-immat.-BALB/c), Dendritic cell (mouse-immat.-C57BL/6), Dendritic cell (mouse-mature-BALB/c), Dendritic cell (mouse-mature-C57BL/6), Dendritic cell (plasmacytoid-human), Dendritic cell (rhesus macaque), DEV, DHL4, DHL6, DLD-1, DO11.10, DOHH-2, Dorsal root gang. (DRG), Dorsal root gang. (DRG) (rat), Dorsal root gang. (DRG) (chicken), Dorsal root gang. (DRG) (mouse), DOV13, DPK, DT40, DU 145, EAhy926, eCAS, ECC-1, EcR293, ECV304, *Eimeria Tenella*, EJM, EL4, Embryonic fibroblast, Embryonic fibroblast (chicken), Embryonic fibroblast (mouse (MEF) immort), Embryonic fibroblast (mouse (MEF) primary), Embryonic stem (ES) cell (human), Embryonic stem (ES) cell (mouse), EMC, Endothelial, Endothelial-aortic-cow (bAEC), Endothelial-aortic-human (HAEC), Endothelial-aortic-pig, Endothelial-coronary art-human (HCAEC), Endothelial-lung-sheep, Endothelial-Mammary-Human, Endothelial-MV dermal-human adult, Endothelial-MV dermal-human neo, Endothelial-MV lung-human (HMVEC-L), Endothelial-pulmonary artery-human, Endothelial-umbilical vn-human (HUVEC), EpH4, Epithilial, Epithelial model-cornea-human-immort., Epithelial-airway-human, Epithelial-airway-pig, Epithelial-alveolar-rat, Epithelial-bronchial (NHBE)-human, Epithelial-bronchial-monkey, Epithelial-cornea-human, epithelial-ES-derived-human, Epithelial-lung type II-human, Epithelial-mammary-human (HMEC), Epithelial-mammary-mouse, Epithelial-prostate (PrEC)-human, Epithelial-renalhuman (HRE), Epithelial-retinal pigment-human, Epithelial-Small Airway-human (SAEC), ESS-1, F36P, F9, FaO, FDC-P1, FDCP-Mix, Fibroblast, Fibroblast-aortic adventitial-human, Fibroblast-cardiac-rat, Fibroblast-cow, Fibroblast-dermal (NHDF-Neo)-human neo, Fibroblast-dermal (NHDF-Ad)-human adult, Fibroblast-dermal-human, Fibroblast-dermalmacaque, Fibroblast-ES-derived-human, Fibroblast-foreskin-human, Fibroblast-humanGM06940, Fibroblast-lung-human normal (NHLF), Fibroblast-lung-mouse, Fibroblast-lungrat, Fibroblast-pig, Fibroblast-tunica albuginea-human, FL5.12A, FM3A, FRT, G-361, GaMG, GD25, GH3, GIST882, GM00131, GM05849, GM09582, Granta519, Granule cell, Granule cell (CGC)-mouse, Granule cell (CGC)-rat, GT1-7, H2K mdx, H4, H4IIE, H69, H9, H9c2(2-1), HaCaT, HC11, HCA7, HCC1937, HCC1954, HCT 116, HCT15, HDLM-2, HDQ-P1, HEL 92.1.7, HeLa, HeLa S3, Hep G2, Hep1B, HEPA 1-6, Hepa-1c1c7, Hepatocyte, Hepatocyte immortalized-mouse, Hepatocyte-human, Hepatocyte-mouse, Hepatocyte-rat, HFF-immort., HFF-1, HFFF2, HIB1B, High Five, HK-2, HL-1, HL-60, HMC-1, HMEC-1, HMLE, HMy2.CIR (C1R), HN5, HPB-ALL, Hs 181.Tes, Hs 578T, HT-1080, HT-29, HT22, HT29-D4, HTC, HU609, HuH7, HuT 102, HuT 78, HUV-EC-C, IEC-6, IEC18, IGROV1, IHH, IM9, IMR-32, IMR-90, INS-1, INS-1E, INS1 832/13, IOSE29, IOSE80, iPS-human, J-774, J-Lat 6.2, J558L, J774A.1, JB6-1, JB6-2, JeKo-1, Jurkat, Jurkat-modified, JVM, JVM-2, K-562, Karpas 299, KE-37, Kelly, Keratinocyte, Keratinocyte-(NHEK-Ad) human adult, Keratinocyte-(NHEK-neo) human neonatal, KG-1, KG-1a, KHYG1, KIT225, KM-H2, KS, KTA2, Ku812, L-428, L1.2, L1210, L1236, L3.6SL, L5178Y, L540, L6, L87/4, LA-N-2, LA-N-5, LAMA-84, Langerhans cells, Langerhans cells-human, LAZ 221, LbetaT2, LCL, *Leishmania tarentolae*, LLC-MK2, LLC-PK1, LLC-PK10, LN229, LNC, LNCaP, LoVo, LP1, LS180, LX-2, LY2, M-07e, M28, MA 104, Macrophage, Macrophage-human, Macrophage-mouse, Macrophage-mouse-BALB/c, Macrophage-mouse-C57BL/6, MC-38, MC/9, MC3, MC3T3, MC3T3-E1, MC57G, McA-RH7777, MCF10, MCF10A, MCF7, MCF7 tet, MCT, MDA-MB-231, MDA-MB-361, MDA-MB-415, MDA-MB-453, MDA-MB-468, MDBK, MDCK, MDCK II, MDCK-C7, ME-1, MedB1, MEG-01, MEL, melan-a, Melanocyte, Melanocyte-(NHEM-neo)-human neonatal, Mesangial cells-Human (NHMC), Mesench. stem (MSC)-pig, Mesenchymal stem cells, Mesenchymal stem cell (MSC)-human, Meso17, Met-1fvb2, MEWO, MFM223, MG-63, MGR3, MHP36, MiaPaCa-2, mIMCD3, MIN6, Mino, MKN-1, mlEND, MLO-Y4, MLP29, MM.1S, MN9D, MOLM-14, MOLT-4, Molt16, Monocyte, MonoMac1 [MM1], MonoMac6 [MM6], Mouse L cell, MPC-11, Mpf, mpkCCD(c14), MPRO, MRC-5, MT4, MTC, MTLn3, Mutu1, MUTZ-2, MUTZ3, MV-4-11, Myoblast, Myoblast-(HSMM) human, Myofibroblast, Myofibroblast-human hepatic, Myofibroblast-rat hepatic, MzCHA-1, N11, N114P2, N1E115, N9, NALM-6, Namalwa, Natural killer (NK)-human, NB-4, NBL-6, NCEB-1, NCI-H1299 [H1299], NCI-H1435, NCI-H2170, NCI-H226 [H226], NCI-H292, NCI-H295R [H295R], NCIH358 [H-358; H358], NCI-H460 [H460], NCI-H69 [H69], NCI-H929 [H929], NCM460, NCTC clone 929, Neural precursor-cow, Neural stem cell (NSC), Neural stem cell (NSC)-human, Neural stem cell (NSC)-mouse, Neural stem cell (NSC)-rat, Neuro-2a [N2a], Neuroblastoma, Neuron-cortical-mouse, Neuron-hippo/cortical-rat, Neuron-hippocampal-chicken, Neuronhippocampal-mouse, Neuron-mesencephalic-rat, Neuron-striatal-mouse, Neuron-striatal-rat, NG108-15, NIH/3T3, NK-92, NK3.3, NKL, NKL1, NRK, NRK-49F, NRK52E, NS0, NS1, NSC34, NTERA-2 cl.D1, OCI-AML1a, OCI-AML2, OCI-AML3, OCI-LY-10, OCI-LY-3, Olfactory neuron-rat, Oligodendrocyte-rat, OP-6, OVCAR3, *P. knowlesi*, P19, P3X63Ag8, P815, PAC2, Pam212, PANC-1, Panc89, PBMC-human, PC-12, PC-3, *Perkinsus marinus, Plasmodium berghei, Plasmodium falciparum, Plasmodium yoelii*, PLB-985, PMC42, Podocytemouse, PS1, PtK1, R28, R9ab, RAEL, RAG2–/–R2BM3-7, Raji, Ramos, Rat2, RAW 264.7, RBL, RBL-1, RBL-2H3, RCC26, RD, REH, Renal Cell Carcinoma, Renal proximal tubule cellshuman, RF/6A, RFL-6, Rh4, Rin 1046, RIN m5f, RKO, RL-952, RMAS, RPMI8226, RS4-11, RT4, RWPE-1, S1A.TB.4.8.2, S49, SA1N, SAM-19, Saos-2, SbC12, Schneider's *Drosophila* Line 2, Schwannoma cell line, SCI-ET27, SCID.adh, SET-2, Sf9 (ovarian), Sf9 (ovarian), SGHPL-4, SH-SYSY, SIRC, SK-BR-3, SK-MEL 100, SK-MEL 103, SK-MEL 147, SK-MEL 173, SK-MEL 187, SK-MEL 19, SK-MEL 192, SK-MEL 197, SK-MEL 23, SK-MEL 29, SKMEL 31, SK-MEL 85, SK-MEL 94, SK-MEL-28, SK-MEL-5, SK-N-AS, SK-N-DZ, SK-N-FI, SK-N-MC, SK-N-SH, SK-OV-3, Skeletal muscle-(SkMC) human, SKNAS, SKW6.4, SMCairway (HASM)-human, SMC-aortic (AoSMC)-human, SMC-aortic (AoSMC)-mouse, SMCaortic (AoSMC)-pig, SMC-aortic (AoSMC)-rat, SMC-bladder (BdSMC)-human, SMCbronchial-human normal (BSMC), SMC-cervix-human, SMC-coronary artery-human (CASMC), SMC-coronary-rat, SMC-pul.artery (PASMC)-human, SMC-rat, SMC-ureterhuman, SMC-uterus-human (UtSMC), SMC-vascular-human, SMC-vascular-monkey, SMCvascular-rat, SP2/0, SP53, Stroco5, SUIT-2, SUM52PE, SUP-T1, SVEC 4-10, SW13, SW1353, SW48, SW480, SW620, SW837, SW872, Synoviocyte-human, SZ95, T cell line-chicken, T cell-human peripheral blood unstim., T cell-human stim., T cell-mouse-BALB/c, T cellmouse-C57BL/6, T cell-rabbit-stimulated, T-47D, T/C-28 a2, T/G HA-VSMC, T0, T1165, T2, T24, T84, TA3, TF-1, TG40, TGW, THP-1, TK6, TOM-1, Tot2, Trabecular meshwork-human, Trabecular meshwork-pig, Trophoblast-human, Trophoblast-mouse, *Trypanosoma brucei, Trypanosoma congolense, Trypanosoma cruzi*, TS/A, TT, Turbinate cell-cow, U-2 OS, U-2940, U-87 MG, U-937, U138MG, U251, U251MG, U266B1, U373, U373MG, U87, UACC903, UMR 106-01, UMSCC-14A, UT7, UT7 GM-CSF dependent, UT7-Epo, UT7-EpoS1, UT7-TPO, V5, V79, VAL, Vero, WEHI-231, WEHI-279, WERI-Rb-1, WI-38, WIL2-S, WM-266-4, WM35, WRO, XG6, XG6, Z-138, Zebrafish cell line, ZF4.

Any suitable cargo may be delivered or extracted from any suitable cells using the present invention. The cargo delivered by the present invention into cells may include, but are not limited to clustered regularly interspaced short palindromic repeats (CRISPR) associated endonuclease (Cas, such as Cas9), transcription activator-like effector nucleases (TALEN), zinc finger nuclease (ZFN), Guide ribonucleic acid (guide RNA), single stranded donor oligonucleotides (ssODN), messenger ribonucleic acid (mRNA), precursor mRNA (pre-mRNA), bacterial artificial chromosome (BACs), peptide nucleic acid (PNA), P-form deoxyribonucleic acid (pDNA), chromosomes, mitochondria, small interfering RNA (siRNA), short hairpin RNA (shRNA), microRNA (miRNA), proteins, morpholinos, metabolites, small molecules, peptides, anitbodies, nanobodies, carbon nanotubes, fluorescent tags and/or dyes, molecular beacons, deoxyribonucleic acid (DNA) origami, nanodevices, microelectromechanical systems (MEMS) devices, polymer constructs including controlled compound release structures (such as polymersome nanoparticles), metal or other functional nanoparticles, nuclei, subcellular organelles, ribozymes, enzymes, microbial pathogens, microbeads, surface Raman-enhanced particles, quantum dots, radionuclide, or magnetic beads. The invention also contemplates the use of episomal vectors.

For example, CRISPR-associated (Cas) proteins may be used in certain embodiments of the invention. Proteins originally found in bacteria in association with clustered, regularly interspersed palindromic repeats (CRISPR) have been dubbed Cas proteins. Cas proteins include Cas9, Cpf1, C2c1, C2c3, and C2c2, and modified versions of Cas9, Cpf1, C2c1, C2c3, and C2c2, such as a nuclease with an amino acid sequence that is different, but at least about 85% similar to, an amino acid sequence of wild-type Cas9, Cpf1, C2c1, C2c3, or C2c2, or a Cas9, Cpf1, C2c1, C2c3, or C2c2 protein. Of those, Cas9 was initially identified as an RNA-guided endonuclease that complexes with both a trans-activating RNA (tracrRNA) and a CRISPR-RNA (crRNA), and is guided by the crRNA to an approximately 20 base target within one strand of double-stranded DNA (dsDNA) that is complementary to a corresponding portion of the crRNA, after which the Cas9 endonuclease creates a double-stranded break in the dsDNA. Cas9 endonuclease is one example among a number of homologous Cas endonucleases that similarly function as RNA-guided, sequence-specific endonucleases. Some variants of Cas endonucleases in which an active site is modified by, for example, an amino acid substitution, have been found to be catalytically inactive, or "dead", Cas (dCas) proteins and function as RNA-guided DNA-binding proteins.

Cas endonucleases and dCas proteins are understood to work with tracrRNA and crRNA or with a single guide RNA (sgRNA) oligonucleotide that includes both the tracrRNA and the crRNA portions and, as used herein, "guide RNA" includes any suitable combination of one or more RNA oligonucleotides that will form a ribonucleoprotein (RNP) complex with a Cas protein or dCas protein and guide the RNP to a target of the guide RNA. The guide RNAs typically include a targeting portion of about 20 bases which will hybridize to a complementary target in dsDNA, when that target is adjacent a short motif dubbed the protospacer-adjacent motif (PAM), to thereby bind the RNP to the dsDNA. When dCas protein is linked to an effector domain and complexed with guide RNA, the resultant complex can upregulate or downregulate transcription. When the target of the guide RNA is within a promoter, the linked effector domain can recruit RNA polymerase or other transcription factors that ultimately recruit the RNA polymerase, which RNA polymerase then transcribes the downstream gene into a primary transcript such as a messenger RNA (mRNA). Such a use of dCas protein to modulate transcription may be exploited to assay for which guide RNAs initiate transcription that results in a particular cellular phenotype and, by mapping a target of those guide RNAs to a particular locus in a reference genome, to identifier promoters at which to regulate transcription to direct a cell to the particular cellular phenotype.

Introducing the dCas proteins and delivering the guide RNAs may be done as a single step by providing the stem cell with a ribonucleoprotein (RNP) comprising the dCas protein linked to the transcription regulator and complexed with the guide RNA. The stem cells may be stimulated to take up the formed RNP using a technique such as electroporation, nanoparticle transfection, or preferably laser excitation of plasmonic substrates. Optionally, introducing the dCas proteins and delivering the guide RNAs includes providing the stem cells with: an mRNA encoding a fusion protein that includes the dCas protein and the transcription regulator; and at least one of the guide RNAs. In some embodiments, introducing the dCas proteins includes delivering a vector comprising a gene for a fusion protein that includes the dCas protein and the transcription regulator. The vector (e.g., a plasmid or viral vector) may be constitutively expressed in the stem cells. The vectors may be introduced into the stem cells by transfection or transduction.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. An intracellular delivery system comprising:
    a laser-activated surface;
    cells positioned at a distance from the laser-activated surface;
    a laser providing a laser pulse that enables the cells to import or export cargo from or to a medium surrounding the cells; and
    contrast-agent microbubbles.

2. The intracellular delivery system of claim 1, wherein the cells flow into and out of a space adjacent to the laser-activated surface.

3. The intracellular delivery system of claim 1, wherein the cells flow in a continuous flow.

4. The intracellular delivery system of claim 1, wherein the cells are stationary.

5. The intracellular delivery system of claim 1, wherein the imported cargo is initially confined to a layer within liquid adjacent to the laser-activated surface and adjacent to a cell layer.

6. The intracellular delivery system of claim 1, wherein the laser-activated surface is selectively targeted to porate specific cells.

7. The intracellular delivery system of claim 6, wherein the laser-activated surface is spatially targeted.

8. The intracellular delivery system of claim 6, wherein the laser-activated surface is temporally targeted.

9. The intracellular delivery system of claim 1, wherein transport of cargo into or out of the cells subsequent to poration is further promoted by application of additional laser pulses, electric fields, turbulent flow, or thermal pulses.

10. The intracellular delivery system of claim 1, wherein the contrast-agent microbubbles are added to the medium surrounding the cells.

11. The intracellular delivery system of claim 1, wherein the laser pulse is provided by an optical source comprising diode-pumped solid state lasers, lamp-pumped solid state lasers, gas lasers, fiber lasers, diode lasers, or quantum cascade lasers.

12. The intracellular delivery system of claim 1, wherein the laser pulse is provided by a continuous wave laser.

13. The intracellular delivery system of claim 1, wherein the laser pulse is produced from a Q-switched light source, a directly modulated light source, a chopped light source, or a redirected light source.

14. The intracellular delivery system of claim 1, wherein the cargo is selected from the group consisting of clustered regularly interspaced short palindromic repeats (CRISPR) associated endonuclease Cas, Cas9, dCas, Cas9 ribonucleoprotein (RNP), dCas RNP, episomal vectors, transcription activator-like effector nuclease (TALEN), zinc finger nuclease (ZFN), guide ribonucleic acid (RNA), single-stranded oligodeoxynucleotide (ssODN), messenger RNA (mRNA), precursor mRNA (pre-mRNA), bacterial artificial chromosome (BAC), peptide nucleic acid (PNA), P-form deoxyribonucleic acid (pDNA), chromosomes, mitochondria, small interfering RNA (siRNA), short hairpin RNA (shRNA), microRNA (miRNA), proteins, morpholinos, metabolites, small molecules, peptides, antibodies, nanobodies, carbon nanotubes, fluorescent tags, fluorescent dyes, molecular beacons, deoxyribonucleic acid (DNA) origami, nanodevices, microelectromechanical systems (MEMS) devices, polymer constructs, controlled compound release structures, metal nanoparticles, functional nanoparticles, nuclei, subcellular organelles, ribozymes, enzymes, microbial pathogens, microbeads, surface Raman-enhanced particles, quantum dots, radionuclide, and magnetic beads.

15. The intracellular delivery system of claim 1, wherein the laser-activated surface comprises a patterned layer of material selected from the group consisting of a thin layer of metal, polymer materials, ink-containing polymers, and an oxide layer.

16. The intracellular delivery system of claim 15, wherein the patterned layer of material comprises the thin layer of metal, wherein the metal is gold.

17. The intracellular delivery system of claim 1, wherein the laser-activated surface is spatially patterned with features.

18. The intracellular delivery system of claim 17, wherein the features promote nucleation of bubbles responsive to absorbing radiation from the laser pulse.

19. The intracellular delivery system of claim 18, wherein the features promote the nucleation of the bubbles at predetermined sites responsive to absorbing the radiation from the laser pulse.

20. An intracellular delivery system comprising:
a laser-activated surface;
cells positioned at a distance from the laser-activated surface;
a laser providing a laser pulse that enables the cells to import or export cargo from or to a medium surrounding the cells; and
a first set of laser-generated contrast-agent microbubbles and a second set of laser-generated contrast-agent microbubbles, wherein the first set of laser-generated contrast-agent microbubbles is imploded by the second set of laser-generated contrast-agent microbubbles.

* * * * *